United States Patent
Tasaka et al.

(10) Patent No.: US 7,141,598 B2
(45) Date of Patent: Nov. 28, 2006

(54) IMIDAZOLE DERIVATIVES, PRODUCTION METHOD THEREOF AND USE THEREOF

(75) Inventors: Akihiro Tasaka, Suita (JP); Takenori Hitaka, Takarazuka (JP); Nobuyuki Matsunaga, Osaka (JP); Masami Kusaka, Kobe (JP)

(73) Assignee: Takeda Pharmaceutical Company, Ltd., Osaka (JP)

( * ) Notice: Subject to any disclaimer, the term of this patent is extended or adjusted under 35 U.S.C. 154(b) by 221 days.

(21) Appl. No.: 10/416,986

(22) PCT Filed: Nov. 16, 2001

(86) PCT No.: PCT/JP01/10002

§ 371 (c)(1),
(2), (4) Date: May 16, 2003

(87) PCT Pub. No.: WO02/40484

PCT Pub. Date: May 23, 2002

(65) Prior Publication Data

US 2004/0033935 A1    Feb. 19, 2004

(30) Foreign Application Priority Data

Nov. 17, 2000 (JP) ............... 2000-351780
Aug. 17, 2001 (JP) ............... 2001-247618
Nov. 1, 2001 (JP) ............... 2001-336880

(51) Int. Cl.
*A61K 31/4184* (2006.01)
*C07D 235/02* (2006.01)

(52) U.S. Cl. .................. 514/393; 548/302.7
(58) Field of Classification Search ............ 548/302.7; 514/393

See application file for complete search history.

(56) References Cited

U.S. PATENT DOCUMENTS 4,728,645 A * 3/1988 Browne .......... 514/210.16
5,057,521 A * 10/1991 Hausler et al. .......... 514/300
5,491,161 A    2/1996 Janssen et al. .......... 514/394

FOREIGN PATENT DOCUMENTS

| EP | 0260744 | 3/1988 |
|---|---|---|
| EP | 0288053 | 10/1988 |
| EP | 0413270 | 2/1991 |
| EP | 0721943 | 7/1996 |
| EP | 0974584 | 1/2000 |
| EP | 1028110 | 8/2000 |
| WO | WO 92/15404 | 9/1992 |
| WO | WO 93/15079 | 8/1993 |
| WO | WO 94/27989 | 12/1994 |
| WO | WO 96/14090 | 5/1996 |
| WO | WO 97/00257 | 1/1997 |
| WO | WO 93/20097 | 10/1998 |
| WO | WO 99/54309 | 10/1999 |

OTHER PUBLICATIONS

Golub et al., Science, vol. 286, Oct. 15, 1999, pp. 531-537.*

* cited by examiner

*Primary Examiner*—Laura L. Stockton
(74) *Attorney, Agent, or Firm*—Mark Chao; Elaine M. Ramesh

(57) ABSTRACT

The present invention provides a compound having a steroid $C_{17,20}$-lyase-inhibitory activity and useful for the therapy and prophylaxis of tumor such as prostatism, breast cancer and the like, and a method for efficiently separating an optically active compound of this compound from a mixture of optical isomers thereof, a compound of the formula:

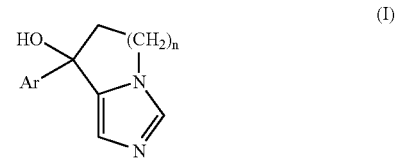

(I)

wherein each symbol is as defined in the specification, a salt thereof or a prodrug thereof, and a method for obtaining an optically active compound by optically resolving a mixture of optical isomers by the use of a resolving agent such as tartranilic acid and the like.

21 Claims, No Drawings

IMIDAZOLE DERIVATIVES, PRODUCTION METHOD THEREOF AND USE THEREOF

TECHNICAL FIELD

This application is the National Phase filing of International Patent Application No. PCT/JP01/10002, filed 16 Nov. 2001.

The present invention relates to a pharmaceutical, among others, a novel condensed imidazole derivative having an inhibitory activity on steroid $C_{17,20}$-lyase, a salt thereof and a prodrug thereof, and to a pharmaceutical composition containing the same. The present invention also relates to a method for producing an optically active compound from an optical isomeric mixture of a novel condensed imidazole derivative, by the use of an optical resolution reagent, and a diastereomeric salt produced during its process. The present invention further relates to a method for asymmetric synthesis that efficiently synthesizes an optically active compound of a novel imidazole or condensed imidazole derivative.

BACKGROUND ART

Androgen and estrogen, which are sex hormones, show a great diversity of physiological activities inclusive of differentiation and proliferation of cells. On the other hand, it has been clarified that androgen and estrogen act as an exacerbation factor in certain diseases. It is known that steroid $C_{17,20}$-lyase is responsible for the final stage of the biosynthesis of androgen in the body. That is, steroid $C_{17,20}$-lyase produces dehydroepiandrosterone and androstenedione using, as a substrate, 17-hydroxypregnenolone and 17-hydroxyprogesterone, which are generated by cholesterol. Therefore, a pharmaceutical agent inhibiting steroid $C_{17,20}$-lyase suppresses production of androgen, as well as production of estrogen synthesized using androgen as a substrate. Such pharmaceutical agent is useful as an agent for the prevention and therapy of diseases wherein androgen and estrogen are exacerbation factors. Examples of the diseases, in which androgen or estrogen is an exacerbation factor, include prostate cancer, prostatic hypertrophy, masculinism, hypertrichosis, male-type baldness, male infant-type prematurity, breast cancer, uterine cancer, ovarian cancer, mastopathy, hysteromyoma, endometriosis, adenomyosis of uterus, polycystic ovary syndrome and the like.

Steroid type compounds and non-steroid type compounds are already known as steroid $C_{17,20}$-lyase inhibitors. Steroid type compounds are disclosed in, for example, WO92/15404, WO93/20097, EP-A-288053, EP-A-413270 and the like. As non-steroid type compounds, for example, JP-A-64-85975 discloses (1H-imidazol-1-yl)methyl-substituted benzimidazole derivatives, WO94/27989, WO96/14090 and WO97/00257 disclose carbazole derivatives, WO95/09157 discloses azole derivatives, U.S. Pat. No. 5,491,161 discloses 1H-benzimidazole derivatives and WO99/18075 discloses dihydronaphthalene derivatives.

In general terms, when a compound contained in a pharmaceutical preparation as an active ingredient has an optical isomer, pharmacological actions and pharmacokinetics may be different depending on optical isomers. In this case, only one of the optical isomers is used as an active ingredient for the purpose of potentiating the activity, and therefore, for reducing the dose, or avoiding unpreferable side effects and the like. For this end, a method for selectively and efficiently producing an optically active compound is desired, wherein the most convenient method is optical resolution of racemate by liquid chromatography using an optically active column filler. When the objective compound is a basic or acidic compound, optical resolution comprising forming a diastereomeric salt by an acid-base reaction with an optically active acid or amine, and separating the salt based on the differences in properties of the both is known to be one of the industrial methods, because this method can achieve a high optical purity comparatively easily and affords production in a large scale.

The optically active acid and amine used here are reported in number as optical resolution reagents. Tartaric acid monoanilides as acidic optical resolution reagent are among them and are known to be effective for optical resolution of many basic compounds [J. Org. Chem., 33, 3993 (1968), JP-A-50-41870, JP-A-51-54566, JP-A-61-7238, JP-A-4-108773, JP-A-5-32620, JP-A-6-100502, JP-A-6-107602, JP-A-6-107604 and the like]. Tartaric acid monoanilide derivatives can be prepared by, for example, the methods described in J. Am. Chem. Soc., 70, 1352 (1948), J. Org. Chem., 33, 3993 (1968), JP-A-10-218847, JP-A-2001-89431 and the like.

DISCLOSURE OF INVENTION

Heretofore, there has not been obtained a steroid $C_{17,20}$-lyase inhibitor applicable to clinical situations, and early development of a steroid $C_{17,20}$-lyase inhibitor highly useful as a pharmaceutical is desired. It is therefore an object of the present invention to provide a steroid $C_{17,20}$-lyase inhibitor highly useful as a pharmaceutical and a compound useful as an active ingredient of such inhibitor. The present invention also aims at providing a method for efficiently separating an optically highly pure compound expected to provide a high effect, from an optical isomer mixture thereof, and providing an optically active compound by the separation. The present invention also aims at provision of a method for efficiently synthesizing a desired optical isomer.

The present inventors have conducted intensive studies in an attempt to find a superior steroid $C_{17,20}$-lyase inhibitor and found that a compound of the formula (I) unexpectedly has a superior pharmaceutical use, particularly a superior steroid $C_{17,20}$-lyase-inhibitory activity, and shows less toxicity and superior properties as a pharmaceutical product, based on its unique chemical structure. Furthermore, they have found a method for separating an optically active compound from a mixture of optical isomers of the compound of the formula (I) by the use of an optically active acid, based on which findings the present invention has been completed.

Accordingly, the present invention provides the following.

[1] A compound of the formula:

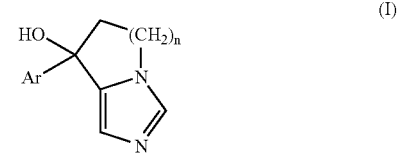

wherein
n is an integer of 1 to 3; and

Ar is an optionally substituted aromatic ring, or a salt thereof.

[2] The compound of [1] above, wherein Ar is an optionally substituted monocyclic or bicyclic aromatic condensed ring.

[3] The compound of [1] above, wherein Ar is an optionally substituted aromatic ring consisting of 5 to 10 atoms including 0 to 4 hetero atom(s) as ring constituting atom(s), which ring being bonded to a condensed imidazole ring in the formula (I) by a carbon atom.

[4] The compound of [1] above, wherein Ar is a group of the formula:

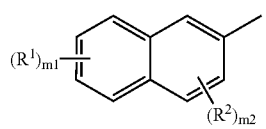
(1)

wherein m1 is an integer of 1 to 4, m2 is an integer of 0 to 3, $R^1$ and $R^2$ are the same or different and each is independently a hydrogen atom, an optionally substituted hydroxyl group, an optionally substituted thiol group, an optionally substituted amino group, an acyl group, a halogen atom or an optionally substituted hydrocarbon group, a group of the formula:

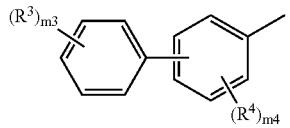
(2)

wherein m3 is an integer of 1 to 5, m4 is an integer of 0 to 4, $R^3$ and $R^4$ are the same or different and each is independently a hydrogen atom, an optionally substituted hydroxyl group, an optionally substituted thiol group, an optionally substituted amino group, an acyl group, a halogen atom or an optionally substituted hydrocarbon group, or a group of the formula:

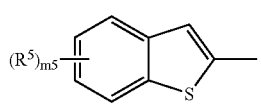
(3)

wherein m5 is an integer of 1 to 4 and $R^5$ is hydrogen atom, an optionally substituted hydroxyl group, an optionally substituted thiol group, an optionally substituted amino group, an acyl group, a halogen atom or an optionally substituted hydrocarbon group.

[5] The compound of [1] above, wherein Ar is a group of the formula:

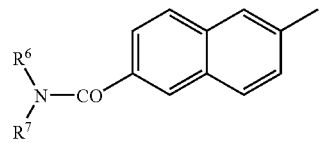
(1-1)

wherein $R^6$ and $R^7$ are the same or different and each is independently a hydrogen atom or a lower alkyl group, or a group of the formula:

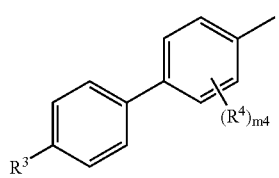
(2-1)

wherein m4 is an integer of 0 to 4, $R^3$ and $R^4$ are the same or different and each is independently a hydrogen atom, an optionally substituted hydroxyl group, an optionally substituted thiol group, an optionally substituted amino group, an acyl group, a halogen atom or an optionally substituted hydrocarbon group.

[6] The compound of [1] above, wherein Ar is a group of the formula:

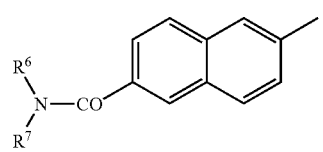
(1-1)

wherein $R^6$ and $R^7$ are the same or different and each is independently a hydrogen atom or lower alkyl group.

[7] The compound of [1] above, wherein the compound of the formula (I) is selected from the group consisting of the following compounds:

(±)-7-(5-methoxybenzo[b]thiophen-2-yl)-6,7-dihydro-5H-pyrrolo[1,2-c]imidazol-7-ol, (±)-7-(5-fluorobenzo[b]thiophen-2-yl)-6,7-dihydro-5H-pyrrolo[1,2-c]imidazol-7-ol, (±)-7-(4'-fluoro[1,1'-biphenyl]-3-yl)-6,7-dihydro-5H-pyrrolo[1,2-c]imidazol-7-ol, (±)-7-(4'-fluoro[1,1'-biphenyl]-4-yl)-6,7-dihydro-5H-pyrrolo[1,2-c]imidazol-7-ol, (±)-6-(7-hydroxy-6,7-dihydro-5H-pyrrolo[1,2-c]imidazol-7-yl)-N-methyl-2-naphthamide, (±)-N-ethyl-6-(7-hydroxy-6,7-dihydro-5H-pyrrolo[1,2-c]imidazol-7-yl)-2-naphthamide, (±)-6-(7-hydroxy-6,7-dihydro-5H-pyrrolo[1,2-c]imidazol-7-yl)-N-isopropyl-2-naphthamide, and (±)-6-(7-hydroxy-6,7-dihydro-5H-pyrrolo[1,2-c]imidazol-7-yl)-2-naphthamide.

[8] The compound of [1] above, which is an enantiomer wherein the steric configuration is an S configuration.

[9] The compound of [1] above, which is an enantiomer wherein the steric configuration is an R configuration.

[10] The compound of [1] above, wherein the compound of the formula (I) is selected from the group consisting of the following compounds:

(±)-7-(4'-fluoro[1,1'-biphenyl]-3-yl)-6,7-dihydro-5H-pyrrolo[1,2-c]imidazol-7-ol, (±)-7-(4'-fluoro[1,1'-biphenyl]-4-yl)-6,7-dihydro-5H-pyrrolo[1,2-c]imidazol-7-ol, (±)-6-(7-hydroxy-6,7-dihydro-5H-pyrrolo[1,2-c]imidazol-7-yl)-N-methyl-2-naphthamide, and (±)-6-(7-hydroxy-6,7-dihydro-5H-pyrrolo[1,2-c]imidazol-7-yl)-2-naphthamide.

[11] The compound of [1] above, wherein the compound of the formula (I) is selected from the group consisting of the following compounds:

(+)-7-(4'-fluoro[1,1'-biphenyl]-3-yl)-6,7-dihydro-5H-pyrrolo[1,2-c]imidazol-7-ol, (−)-7-(4'-fluoro[1,1'-biphenyl]-3-yl)-6,7-dihydro-5H-pyrrolo[1,2-c]imidazol-7-ol, (+)-7-(4'-fluoro[1,1'-biphenyl]-4-yl)-6,7-dihydro-5H-pyrrolo[1,2-c]imidazol-7-ol, (−)-7-(4'-fluoro[1,1'-biphenyl]-4-yl)-6,7-dihydro-5H-pyrrolo[1,2-c]imidazol-7-ol, (+)-6-(7-hydroxy-6,7-dihydro-5H-pyrrolo[1,2-c]imidazol-7-yl)-N-methyl-2-naphthamide, (−)-6-(7-hydroxy-6,7-dihydro-5H-pyrrolo[1,2-c]imidazol-7-yl)-N-methyl-2-naphthamide, (+)-6-(7-hydroxy-6,7-dihydro-5H-pyrrolo[1,2-c]imidazol-7-yl)-2-naphthamide, and (−)-6-(7-hydroxy-6,7-dihydro-5H-pyrrolo[1,2-c]imidazol-7-yl)-2-naphthamide.

[12] A prodrug of the compound of [1] to [11] above.

[13] A pharmaceutical composition containing the compound or a prodrug thereof of [1] to [12] above.

[14] The pharmaceutical composition of [13] above, which is a steroid $C_{17,20}$-lyase inhibitor.

[15] The pharmaceutical composition of [13] above, which is an antitumor agent.

[16] The pharmaceutical composition of [13] above, which is an agent for the prophylaxis or treatment of breast cancer or prostate cancer.

[17] An agent for decreasing androgen containing the compound or a prodrug thereof of [1] to [12] above as an active ingredient, which is used concurrently with an LHRH receptor modulator.

[18] A method for producing a compound of the formula:

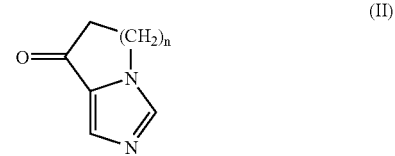

wherein Ar is an optionally substituted aromatic ring and n is an integer of 1 to 3, or salt thereof, which method comprises reacting a compound of the formula:

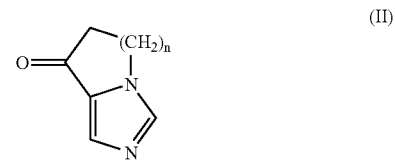

wherein n is as defined above, or a salt thereof and a compound of the formula:

wherein X is a leaving group and Ar is as defined above, or a salt thereof in the presence of a metal or a metal compound.

[19] A method for producing a compound of the formula:

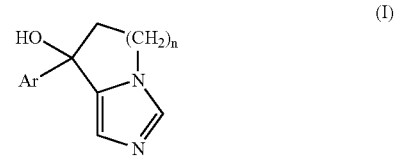

wherein Ar is an optionally substituted aromatic ring and n is an integer of 1 to 3, or a salt thereof, which method comprises reacting a compound of the formula:

wherein X' is hydrogen atom or a leaving group and Ar is as defined above, or a salt thereof, with a metal compound or metal, and then with a compound of the formula:

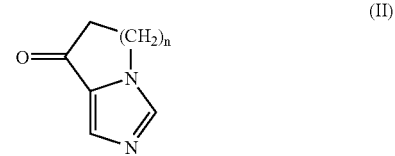

wherein n is as defined above, or a salt thereof.

[20] A method for producing an optically active compound of the compound of the formula (I-1) or a salt thereof, which method comprises reacting a mixture of optical isomers of the compound of the formula:

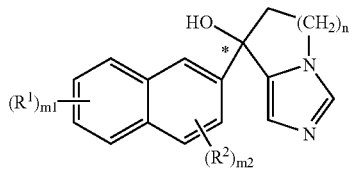

(I-1)

wherein n is an integer of 1 to 3, m1 is an integer of 1 to 4, m2 is an integer of 0 to 3, $R^1$ and $R^2$ are the same or different and each is independently a hydrogen atom, an optionally substituted hydroxyl group, an optionally substituted thiol group, an optionally substituted amino group, an acyl group, a halogen atom or an optionally substituted hydrocarbon group, and * shows the position of an asymmetric carbon, with an optically active compound of the compound of the formula:

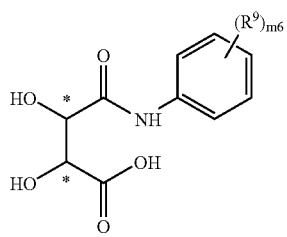

(IV)

wherein each $R^9$ is the same or different and is a hydrogen atom, $C_{1-3}$ alkyl group, $C_{1-3}$ alkoxy group, a hydroxyl group, a nitro group, a halogen atom such as a fluorine, a chlorine, a bromine, an iodine and the like, which is substituted at an optional position on a benzene ring, m6 is an integer of 0 to 3, and * shows the position of an asymmetric carbon, to give a diastereomeric salt, separating the obtained diastereomeric salt and isolating an optically active compound of the compound of the formula (I-1).

[21] The method of [20] above, wherein the compound of the formula (IV) is tartranilic acid of the following formula:

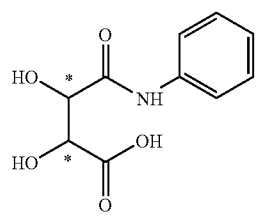

(IV-1)

wherein * shows the position of an asymmetric carbon.

[22] The method of [20] above, wherein the mixture of the optical isomer of the formula (I-1) is that represented by the following formula:

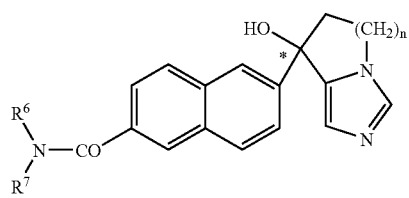

(I-2)

wherein n is an integer of 1 to 3, $R^6$ and $R^7$ are the same or different and each is independently a hydrogen atom or a lower alkyl group and * shows the position of an asymmetric carbon.

[23] A diastereomeric salt of a compound of the formula (I-1) and a compound of the formula (IV).

[24] A diastereomeric salt of a compound of the formula (I-2) and a compound of the formula (IV).

[25] A diastereomeric salt of 6-(7-hydroxy-6,7-dihydro-5H-pyrrolo[1,2-c]imidazol-7-yl)-N-methyl-2-naphthamide and an optically active tartranilic acid.

[26] A salt of (+)-6-(7-hydroxy-6,7-dihydro-5H-pyrrolo[1,2-c]imidazol-7-yl)-N-methyl-2-naphthamide and (2S,3S)-(−)-tartranilic acid.

[27] A pharmaceutical composition containing, as an active ingredient, an optically active compound of the compound of the formula (I-1).

[28] A method for producing an optically active compound of the formula:

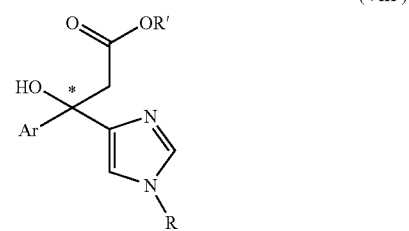

(VIII')

wherein R is a protecting group, Ar is an optionally substituted aromatic ring and R' is a lower alkyl group having 1 to 6 carbon atoms or an arylalkyl group, which method comprises reacting a compound of the formula

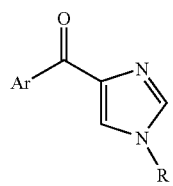

(VII)

wherein each symbol is as defined above, or a salt thereof, with a compound of the formula:

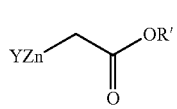 (XI)

wherein Y is a halogen atom, R' is as defined above, in the presence of a chiral ligand.

[29] The method of [28] above, wherein the chiral ligand is cinchona alkaloid.

[30] A compound of the formula:

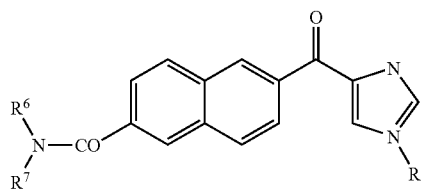 (VII-1)

wherein $R^6$ and $R^7$ are the same or different and each is independently a hydrogen atom or a lower alkyl group and R is a protecting group, or a salt thereof.

[31] A compound of the formula:

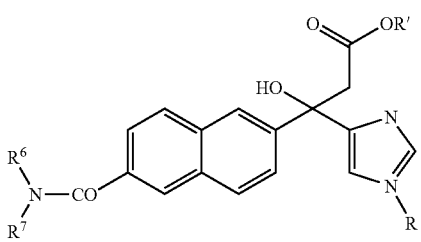 (VIII-1)

wherein $R^6$ and $R^7$ are the same or different and each is independently a hydrogen atom or a lower alkyl group, R is a protecting group and R' is a lower alkyl group having 1 to 6 or an arylalkyl group, or a salt thereof.

[32] A production method of a compound of the formula:

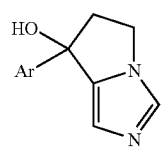 (I-3)

wherein Ar is an optionally substituted aromatic ring, or a salt thereof, which method comprising subjecting a compound of the formula:

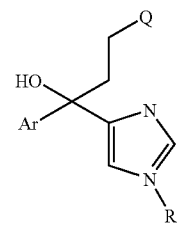 (X)

wherein R is a protecting group, Q is a leaving group and Ar is as defined above, or a salt thereof, to a cyclization reaction.

DETAILED DESCRIPTION OF THE INVENTION

In the specification, each symbol in each formula is defined as follows.

While n is an integer of 1 to 3, it is preferably 1.
While m1 is an integer of 1 to 4, it is preferably 1 or 2, particularly preferably 1.
While m2 is an integer of 0 to 3, it is preferably 0 or 1, particularly preferably 0.
While m3 is an integer of 1 to 5, it is preferably 1 to 3, particularly preferably 1.
While m4 is an integer of 0 to 4, it is preferably 0 or 1, particularly preferably 0.
While m5 is an integer of 1 to 4, it is preferably 1 or 2, particularly preferably 1.
While m6 is an integer of 0 to 3, it is preferably 0 or 1, particularly preferably 0.

The optionally substituted hydroxyl group expressed by $R^1$, $R^2$, $R^3$, $R^4$ and $R^5$ is exemplified by unsubstituted hydroxyl group, lower alkoxy (e.g., $C_{1-4}$ alkoxy group such as methoxy, ethoxy and propoxy), lower alkanoyloxy (e.g., $C_{1-4}$ alkanoyloxy group such as acetyloxy and propionyloxy), optionally substituted carbamoyloxy (e.g., unsubstituted carbamoyloxy, carbamoyloxy substituted by 1 or 2 $C_{1-4}$ alkyl, such as methylcarbamoyloxy, ethylcarbamoyloxy, dimethylcarbamoyloxy, diethylcarbamoyloxy, ethylmethylcarbamoyloxy etc.) and the like.

The optionally substituted thiol group expressed by $R^1$, $R^2$, $R^3$, $R^4$ and $R^5$ is exemplified by unsubstituted thiol group, lower alkylthio (e.g., $C_{1-4}$ alkylthio such as methylthio, ethylthio and propylthio), lower alkanoylthio (e.g., $C_{1-4}$ alkanoylthio group such as acetylthio and propionylthio) and the like.

The optionally substituted amino group expressed by $R^1$, $R^2$, $R^3$, $R^4$ and $R^5$ is exemplified by unsubstituted amino, lower alkylamino (e.g., $C_{1-4}$ alkylamino such as methylamino, ethylamino and propylamino), di(lower alkyl)amino (e.g., di($C_{1-4}$ alkyl)amino such as dimethylamino and diethylamino), $C_{1-4}$ alkanoylamino (e.g., acetylamino, propionylamino, etc.) and the like.

The acyl expressed by $R^1$, $R^2$, $R^3$, $R^4$ and $R^5$ is exemplified by alkanoyl group (e.g., $C_{1-6}$ alkanoyl group such as formyl, acetyl and propionyl), alkylsulfonyl group (e.g., $C_{1-4}$ alkylsulfonyl group such as methylsulfonyl and ethylsulfonyl), aroyl group (e.g., benzoyl, toluoyl, naphthoyl, etc.), an optionally substituted carbamoyl group (e.g., monoor di-$C_{1-10}$ alkylcarbamoyl group such as methylcarbamoyl, ethylcarbamoyl, dimethylcarbamoyl, diethylcarbamoyl; mono- or di-$C_{6-14}$ arylcarbamoyl group such as phenylcarbamoyl and diphenylcarbamoyl; mono- or di-$C_{7-16}$ aralkylcarbamoyl group such as benzylcarbamoyl, dibenzylcarbamoyl etc., and the like), an optionally substituted sulfamoyl group (e.g., mono- or di-$C_{1-10}$ alkylsulfamoyl group such as methylsulfamoyl, ethylsulfamoyl, dimethylsulfamoyl, diethylsulfamoyl and the like, mono- or di-$C_{6-14}$ arylsulfamoyl group such as phenylsulfamoyl, diphenylsulfamoyl and the like, mono- or di-$C_{7-16}$ aralkylsulfamoyl group such as benzylsulfamoyl, dibenzylsulfamoyl etc. and the like) and the like.

The halogen expressed by $R^1$, $R^2$, $R^3$, $R^4$, $R^5$ and Y is exemplified by fluorine, chlorine, bromine and iodine.

The "hydrocarbon group" of the "an optionally substituted hydrocarbon group" expressed by $R^1$, $R^2$, $R^3$, $R^4$ and $R^5$ is exemplified by chain hydrocarbon group or cyclic hydrocarbon group and the like.

Examples of the chain hydrocarbon group include linear or branched chain hydrocarbon group having 1 to 10 carbon atoms and the like, which are specifically alkyl group, alkenyl group and the like. Of these, alkyl is particularly preferable. Examples of the "alkyl" include $C_{1-10}$ alkyl, such as methyl, ethyl, n-propyl, isopropyl, butyl, isobutyl, sec-butyl, tert-butyl, n-pentyl, isopentyl, neopentyl, n-hexyl, isohexyl etc., and the like, with preference given to $C_{1-6}$ alkyl (e.g., methyl, ethyl, n-propyl, isopropyl, n-butyl, sec-butyl, tert-butyl etc.). Examples of the "alkenyl group" include $C_{2-10}$ alkenyl group, such as vinyl, 1-propenyl, allyl, isopropenyl, 1-butenyl, 2-butenyl, 3-butenyl, isobutenyl, sec-butenyl etc., and the like, with preference given to $C_{2-6}$ alkenyl group (e.g., vinyl, 1-propenyl, allyl etc.). Examples of the "alkynyl group" include $C_{2-10}$ alkynyl group, such as ethynyl, 1-propynyl, propargyl etc., and the like, with preference given to $C_{2-6}$ alkynyl group (e.g., ethynyl etc.).

Examples of the cyclic hydrocarbon group include cyclic hydrocarbon group having 3 to 18 carbon atoms, such as alicyclic hydrocarbon group, aromatic hydrocarbon group and the like.

Examples of the "alicyclic hydrocarbon group" include monocyclic group consisting of 3 to 10 carbon atoms and polycyclic condensed ring, such as cycloalkyl group, cycloalkenyl group, and bicyclic or tricyclic condensed ring of these and $C_{6-14}$ aryl (e.g., benzene etc.). Examples of the "cycloalkyl" include $C_{3-6}$ cycloalkyl, such as cyclopropyl, cyclobutyl, cyclopentyl, cyclohexyl etc., and the like and examples of the "cycloalkenyl group" include $C_{3-6}$ cycloalkenyl group, such as cyclopropenyl, cyclobutenyl, cyclopentenyl, cyclohexenyl etc., and the like.

Examples of the "aromatic hydrocarbon group" include monocyclic aromatic hydrocarbon group, condensed polycyclic aromatic hydrocarbon group and the like consisting of 6 to 18 carbon atoms, which are specifically $C_{6-14}$ aryl, such as phenyl, 1-naphthyl, 2-naphthyl, 2-indenyl, 2-anthryl and the like, with preference given to $C_{6-10}$ aryl (e.g., phenyl etc.) and the like.

The substituent that the "chain hydrocarbon group" may have in the "optionally substituted hydrocarbon group" is not subject to any particular limitation. Examples thereof include halogen atom, hydroxyl group, alkoxy group, acyloxy group, alkylthio group, acylamino group, carboxyl group, alkoxycarbonyl group, oxo group, alkylcarbonyl group, cycloalkyl group, aryl group, aromatic heterocyclic group and the like. These substituents are substituted in a chemically acceptable range on the "chain hydrocarbon group", wherein the number of substitution of the substituent is 1 to 5, preferably 1 to 3. When the number of substituent is not less than 2, they may be the same or different.

The substituent that the "cyclic hydrocarbon group" may have in the "optionally substituted hydrocarbon group" is not subject to any particular limitation. Examples thereof include halogen atom, hydroxyl group, alkoxy group, acyloxy group, alkylthio group, alkylsulfonyl group, mono- or di-alkylamino group, acylamino group, carboxyl group, alkoxycarbonyl group, alkynylcarbonyl group, alkyl group, cycloalkyl group, aryl group, aromatic heterocyclic group and the like. These substituents are substituted in a chemically acceptable range on the "cyclic hydrocarbon group", wherein the number of substitution of the substituent is 1 to 5, preferably 1 to 3. When the number of substituent is not less than 2, they may be the same or different.

Examples of the "halogen atom" include fluorine, chlorine, bromine, iodine and the like. Examples of the "alkoxy" include $C_{1-10}$ alkoxy, such as methoxy, ethoxy, propoxy, isopropoxy, butoxy, isobutoxy, sec-butoxy, pentyloxy, hexyloxy etc., and the like. Examples of the "acyloxy group" include formyloxy, $C_{1-10}$ alkyl-carbonyloxy (e.g., acetoxy, propionyloxy etc.) and the like. Examples of the "alkylthio group" include $C_{1-10}$ alkylthio group, such as methylthio, ethylthio, propylthio, isopropylthio etc., and the like. Examples of the "alkylsulfonyl group" include $C_{1-10}$ alkylsulfonyl group, such as methylsulfonyl, ethylsulfonyl, propylsulfonyl etc., and the like. Examples of the "acylamino" include formylamino, diformylamino, mono- or di-$C_{1-10}$ alkyl-carbonylamino (e.g., acetylamino, propionylamino, butyrylamino, diacetylamino etc.) and the like. Examples of the "mono- or di-alkylamino" include those similar to the aforementioned lower alkylamino and di(lower)alkylamino. Examples of the "alkoxycarbonyl group" include $C_{1-10}$ alkoxy-carbonyl group, such as methoxycarbonyl, ethoxycarbonyl, propoxycarbonyl, isopropoxycarbonyl, butoxycarbonyl etc., and the like. Examples of the "alkylcarbonyl group" include $C_{1-10}$ alkyl-carbonyl group, such as acetyl, propionyl, butyryl, valeryl etc., and the like. Examples of the "alkynylcarbonyl group" include $C_{3-10}$ alkynylcarbonyl group, such as ethynylcarbonyl, 1-propynylcarbonyl, 2-propynylcarbonyl etc., and the like. Examples of the "cycloalkyl" include $C_{3-10}$ cycloalkyl, such as cyclopropyl, cyclobutyl, cyclopentyl, cyclohexyl etc., and the like. Examples of the "aryl" include $C_{6-14}$ aryl, such as phenyl, 1-naphthtyl, 2-naphthtyl etc., and the like. Examples of the "aromatic heterocyclic group" include mono-, di- or tricyclic aromatic heterocyclic group containing, besides the carbon atom, 1 or 2 kinds of hetero atom, preferably 1 to 4 hetero atoms selected from nitrogen, oxygen and sulfur, and the like. Specifically, for example, thienyl, pyridyl, furylpyrazinyl, pyrimidinyl, imidazolyl, pyrazolyl, thiazolyl, isothiazolyl, oxazolyl, isoxazolyl, pyridazinyl, tetrazolyl, quinolyl, indolyl, isoindolyl and the like are mentioned. Examples of the "alkyl" include $C_{1-10}$ alkyl, such as methyl, ethyl, propyl, isopropyl, butyl, sec-butyl, tert-butyl, pentyl etc., and the like.

The substituent that the aforementioned "hydrocarbon group" may have optionally has 1 to 5, preferably 1 to 3, substituents shown below in a chemically acceptable range. Examples of the substituent include halogen atom (e.g., fluorine, chlorine, bromine etc.), hydroxyl group, $C_{1-6}$ alkoxy group (e.g., methoxy, ethoxy, propoxy, isopropoxy, etc.), and the like.

Examples of the lower alkyl group expressed by $R^6$ and $R^7$ include linear, branched or cyclic alkyl having 1 to 4 carbon atoms, which are specifically methyl, ethyl, n-propyl, isopropyl, butyl, isobutyl, sec-butyl, tert-butyl, cyclopropyl, cyclobutyl and the like.

Examples of the $C_{1-3}$ alkyl expressed by $R^9$ include linear or branched alkyl having 1 to 3 carbon atoms, which are specifically methyl, ethyl, n-propyl, isopropyl and the like.

Examples of the $C_{1-3}$ alkoxy expressed by $R^9$ include linear or branched alkoxy having 1 to 3 carbon atoms, which are specifically methoxy, ethoxy, n-propoxy, isopropoxy and the like.

The protecting group of the imidazole ring at R may be, for example, amino-protecting group, which is specifically $C_{7-10}$ aralkyloxymethyl (e.g., benzyloxymethyl etc.), $C_{1-6}$ alkylcarbonyloxymethyl (e.g., tert-butylcarbonyloxymethyl etc.), $C_{6-12}$ arylsulfonyl (e.g., p-toluenesulfonyl etc.), di-$C_{1-4}$ alkylaminosulfonyl, trityl and the like, each being optionally substituted, and formyl. Preferably, it is a benzyloxymethyl group and a trityl group. The substituents for these may be halogen atom (e.g., fluorine, chlorine, bromine, iodine etc.), $C_{1-6}$ alkyl-carbonyl (e.g., acetyl, propionyl, valeryl etc.), nitro group and the like, wherein the number of substituents is about 1 to 3.

Examples of the lower alkyl group having 1 to 6 carbon atom at R' include linear, branched or cyclic alkyl group having 1 to 6 carbon atoms, which is specifically methyl, ethyl, n-propyl, isopropyl, butyl, isobutyl, sec-butyl, tert-butyl, cyclopropyl, cyclobutyl and the like.

The arylalkyl group at R' may be benzyl and the like.

Examples of the leaving group at X include halogen atom (chlorine atom, bromine atom, iodine atom etc.), alkyl or arylsulfonyloxy group (methanesulfonyloxy, ethanesulfonyloxy, trifluoromethanesulfonyloxy, benzenesulfonyloxy, p-toluenesulfonyloxy etc.) and the like.

The leaving group at Q is exemplified by those mentioned with regard to the above-mentioned X.

The optionally substituted aromatic ring represented by Ar is exemplified by one or more optionally substituted monocyclic or bicyclic aromatic condensed ring(s) and the like. Ar is preferably exemplified by an optionally substituted aromatic ring consisting of 5 to 10 atoms including 0 to 4 hetero atom(s) as ring constituting atom(s), wherein the aromatic ring is bonded to a condensed imidazole ring in the formula (I) not by a hetero atom but by a carbon atom.

The substituents for the an optionally substituted aromatic ring represented by Ar is exemplified by optionally substituted hydroxyl group, optionally substituted thiol group, optionally substituted amino group, acyl group, halogen atom and optionally substituted hydrocarbon group. The "optionally substituted hydroxyl group", "optionally substituted amino group", "acyl group", "halogen atom" and "optionally substituted hydrocarbon group" are each exemplified by those mentioned with regard to the above-mentioned $R^1$, $R^2$, R $R^4$ and $R^5$.

In the formula (I), Ar is preferably a group of the formula (1) and a group of the formula (2), particularly preferably a group of the formula (1). Of the groups of the formula (1), a group of the formula (1-1) is more preferable, and of the groups of the formula (1-1), a group wherein both $R^6$ and $R^7$ are hydrogen atoms and a group, wherein one of them is hydrogen and the other is methyl group or ethyl group, is particularly preferable.

Of the groups of the formula (2), a group of the formula:

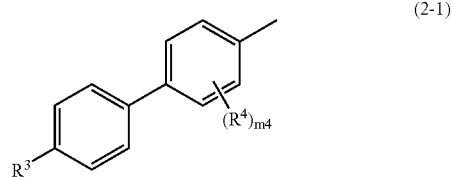

(2-1)

wherein each symbol is as defined above, is more preferable, and of the groups of the formula (2-1), a group wherein m4 is 0 and $R^3$ is halogen atom is particularly preferable.

Preferable examples of the compound (I) of the present invention include the following compounds:
(±)-7-(5-methoxybenzo[b]thiophen-2-yl)-6,7-dihydro-5H-pyrrolo[1,2-c]imidazol-7-ol,
(±)-7-(5-fluorobenzo[b]thiophen-2-yl)-6,7-dihydro-5H-pyrrolo[1,2-c]imidazol-7-ol,
(±)-7-(4'-fluoro[1,1'-biphenyl]-3-yl)-6,7-dihydro-5H-pyrrolo[1,2-c]imidazol-7-ol,
(±)-7-(4'-fluoro[1,1'-biphenyl]-4-yl)-6,7-dihydro-5H-pyrrolo[1,2-c]imidazol-7-ol,
(±)-6-(7-hydroxy-6,7-dihydro-5H-pyrrolo[1,2-c]imidazol-7-yl)-N-methyl-2-naphthamide,
(±)-N-cyclopropyl-6-(7-hydroxy-6,7-dihydro-5H-pyrrolo[1,2-c]imidazol-7-yl)-2-naphthamide,
(±)-N-ethyl-6-(7-hydroxy-6,7-dihydro-5H-pyrrolo[1,2-c]imidazol-7-yl)-2-naphthamide,
(±)-N-cyclobutyl-6-(7-hydroxy-6,7-dihydro-5H-pyrrolo[1,2-c]imidazol-7-yl)-2-naphthamide,
(±)-6-(7-hydroxy-6,7-dihydro-5H-pyrrolo[1,2-c]imidazol-7-yl)-N-isopropyl-2-naphthamide,
(±)-6-(7-hydroxy-6,7-dihydro-5H-pyrrolo[1,2-c]imidazol-7-yl)-2-naphthamide,
(+)-7-(5-methoxybenzo[b]thiophen-2-yl)-6,7-dihydro-5H-pyrrolo[1,2-c]imidazol-7-ol,
(+)-7-(5-fluorobenzo[b]thiophen-2-yl)-6,7-dihydro-5H-pyrrolo[1,2-c]imidazol-7-ol,
(+)-7-(4'-fluoro[1,1'-biphenyl]-3-yl)-6,7-dihydro-5H-pyrrolo[1,2-c]imidazol-7-ol,
(+)-7-(4'-fluoro[1,1'-biphenyl]-4-yl)-6,7-dihydro-5H-pyrrolo[1,2-c]imidazol-7-ol,
(+)-6-(7-hydroxy-6,7-dihydro-5H-pyrrolo[1,2-c]imidazol-7-yl)-N-methyl-2-naphthamide,
(+)-N-cyclopropyl-6-(7-hydroxy-6,7-dihydro-5H-pyrrolo[1,2-c]imidazol-7-yl)-2-naphthamide,
(+)-N-ethyl-6-(7-hydroxy-6,7-dihydro-5H-pyrrolo[1,2-c]imidazol-7-yl)-2-naphthamide,
(+)-N-cyclobutyl-6-(7-hydroxy-6,7-dihydro-5H-pyrrolo[1,2-c]imidazol-7-yl)-2-naphthamide,
(+)-6-(7-hydroxy-6,7-dihydro-5H-pyrrolo[1,2-c]imidazol-7-yl)-N-isopropyl-2-naphthamide,
(+)-6-(7-hydroxy-6,7-dihydro-5H-pyrrolo[1,2-c]imidazol-7-yl)-2-naphthamide,
(−)-7-(5-methoxybenzo[b]thiophen-2-yl)-6,7-dihydro-5H-pyrrolo[1,2-c]imidazol-7-ol,
(−)-7-(5-fluorobenzo[b]thiophen-2-yl)-6,7-dihydro-5H-pyrrolo[1,2-c]imidazol-7-ol,
(−)-7-(4'-fluoro[1,1'-biphenyl]-3-yl)-6,7-dihydro-5H-pyrrolo[1,2-c]imidazol-7-ol,
(−)-7-(4'-fluoro[1,1-biphenyl]-4-yl)-6,7-dihydro-5H-pyrrolo[1,2-c]imidazol-7-ol,
(−)-6-(7-hydroxy-6,7-dihydro-5H-pyrrolo[1,2-c]imidazol-7-yl)-N-methyl-2-naphthamide, (−)-N-cyclopropyl-6-(7-hydroxy-6,7-dihydro-5H-pyrrolo[1,2-c]imidazol-7-yl)-2-naphthamide,
(−)-N-ethyl-6-(7-hydroxy-6,7-dihydro-5H-pyrrolo[1,2-c]imidazol-7-yl)-2-naphthamide,
(−)-N-cyclobutyl-6-(7-hydroxy-6,7-dihydro-5H-pyrrolo[1,2-c]imidazol-7-yl)-2-naphthamide,
(−)-6-(7-hydroxy-6,7-dihydro-5H-pyrrolo[1,2-c]imidazol-7-yl)-N-isopropyl-2-naphthamide, and
(−)-6-(7-hydroxy-6,7-dihydro-5H-pyrrolo[1,2-c]imidazol-7-yl)-2-naphthamide.

The compound of the formula (I) of the present invention may form a salt, which is exemplified by an acid addition salt, such as inorganic acid salts (e.g., hydrochloride, sulfate, hydrobromate, phosphate etc.), organic acid salts (e.g., acetate, trifluoroacetate, succinate, maleate, fumarate, propionate, citrate, tartrate, lactate, oxalate, methanesulfonate, p-toluenesulfonate etc.) and the like.

The compound of the formula (I) and a salt thereof may be hydrates, which are encompassed in the present invention. Hereinafter the compound (I) also includes salts and hydrates.

The prodrug of the compound (I) means a compound that is converted to compound (I) having a steroid $C_{17,20}$-lyase-inhibitory action in the body by reaction with an enzyme, gastric acid and the like.

As the prodrug of the compound (I), a compound wherein an imidazole nitrogen of compound (I) is acylated or alkylated [e.g., dimethylaminosulfonylated, acetoxymethylated, (5-methyl-2-oxo-1,3-dioxolen-4-yl)methoxycarbonylmethylated, pivaloyloxymethylated or benzyloxymethylated compound etc.]; a compound wherein hydroxy of compound (I) is acylated, alkylated, phosphorylated, sulfated, borated [e.g., compound wherein hydroxy of compound (I) is acetylated, palmitoylated, propanoylated, pivaloylated, succinylated, fumalylated, alanylated or dimethylaminomethylcarbonylated etc.], and the like are preferred. These compounds can be produced by a method known per se.

The prodrug of compound (I) may be as it is or a pharmacologically acceptable salt. Examples of such salt include, when the prodrug of compound (I) has an acidic group, such as carboxyl group and the like, salts with inorganic base (e.g., alkali metal such as sodium, potassium and the like, alkaline earth metal such as calcium, magnesium etc., transition metal such as zinc, iron, copper etc., and the like), salts with organic base (e.g., organic amines such as trimethylamine, triethylamine, pyridine, picoline, ethanolamine, diethanolamine, triethanolamine, dicyclohexylamine, N,N'-dibenzylethylenediamine etc., basic amino acids such as arginine, lysine, ornithine etc., etc.), and the like.

When the prodrug of compound (I) has a basic group, such as amino group and the like, the salt is exemplified by salts with inorganic acid and organic acid (e.g., hydrochloric acid, nitric acid, sulfuric acid, phosphoric acid, carbonic acid, bicarbonic acid, formic acid, acetic acid, propionic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid etc.), salts with acidic amino acid, such as aspartic acid, glutamic acid etc., and the like.

The prodrug of compound (I) may be a hydrate or a non-hydrate.

While it has one or more asymmetric carbon(s) in a molecule, both an R configuration compound and an S configuration compound due to the asymmetric carbons are encompassed in the present invention.

As the compound (I), a compound, wherein the absolute configuration of carbon atom bonded to hydroxy is S configuration, is preferable.

Throughout the specification, in the compound represented by each formula, a compound having a basic group or an acidic group can form a salt with an acid addition salt or a salt with a base. The salts with these acid addition salts and bases are exemplified by those recited with regard to the aforementioned compound (I). In the following, the compounds of the respective formulas, inclusive of salts thereof, are to be briefly referred to as a compound (symbol of the formula). For example, a compound of the formula (II) and a salt thereof are simply referred to as compound (II).

The compound (I) can be produced by, for example, the following method and the like.

A starting material compound and a synthetic intermediate can be used in a free form or in the form of a salt as exemplified for compound (I), or subjected to reaction as a reaction mixture or after isolation by a known method.

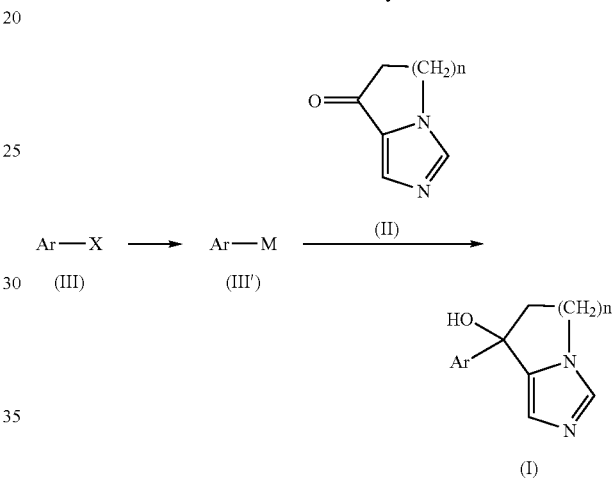

wherein M is a metal or a salt thereof and other symbols are as defined above.

Examples of the metal expressed by M include lithium, magnesium and the like, and examples of the metal salt include metal halide, such as magnesium chloride, magnesium bromide etc., and the like.

The leaving group expressed by X is exemplified by halogen atom (chlorine atom, bromine atom, iodine atom etc.), alkyl or arylsulfonyloxy group (methanesulfonyloxy, ethanesulfonyloxy, trifluoromethanesulfonyloxy, benzenesulfonyloxy, p-toluenesulfonyloxy etc.), and the like.

The compound (III) is converted to organic metal compound (III') by reacting a metal compound, such as alkyl lithium and the like, or a metal, such as magnesium and the like, and reacting with compound (II), whereby compound (I) can be obtained.

Examples of the alkyl lithium to be used in this reaction include $C_{1-4}$ alkyl lithium, such as n-butyl lithium, s-butyl lithium, t-butyl lithium and the like, which is particularly preferably n-butyl lithium. The amount of the alkyl lithium to be used in this reaction is 1 to 2 equivalents, preferably 1 to 1.2 equivalents, of the starting material compound (III). The reaction temperature is from −120° C. to 0° C., preferably from −100° C. to −20° C. The reaction solvent is preferably THF, toluene and the like. When X is a halogen atom, magnesium is reacted to give a Grignard reagent (III'), which is reacted with compound (II). When magnesium is reacted with compound (III), the reaction temperature is from −40° C. to 60° C., preferably from −20° C. to 40° C. The reaction time is from 5 minutes to about 20 hours.

When compound (III') is produced by using alkyl lithium in this reaction, the presence of an anion obtained by reacting alkyl lithium with 2-bromobenzene trifluoride (benzene trifluoride anion) affords increased reaction yield.

For example, the compound (II) can be synthesized according to the following method.

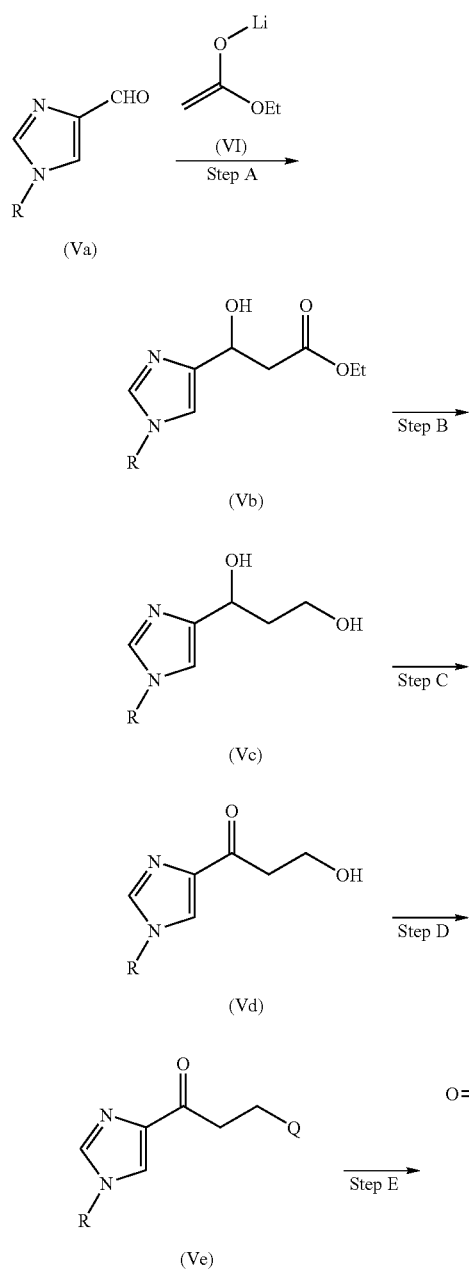

−60° C. After reduction of ester moiety, compound (Vd) can be obtained by the use of an oxidizing agent, such as manganese dioxide and the like. Furthermore, by converting alcohol to a leaving group, such as methanesulfonic acid ester and the like, and a heat treatment in the presence of a base, compound (II) can be obtained.

The compound (II) can be also obtained according to the following method.

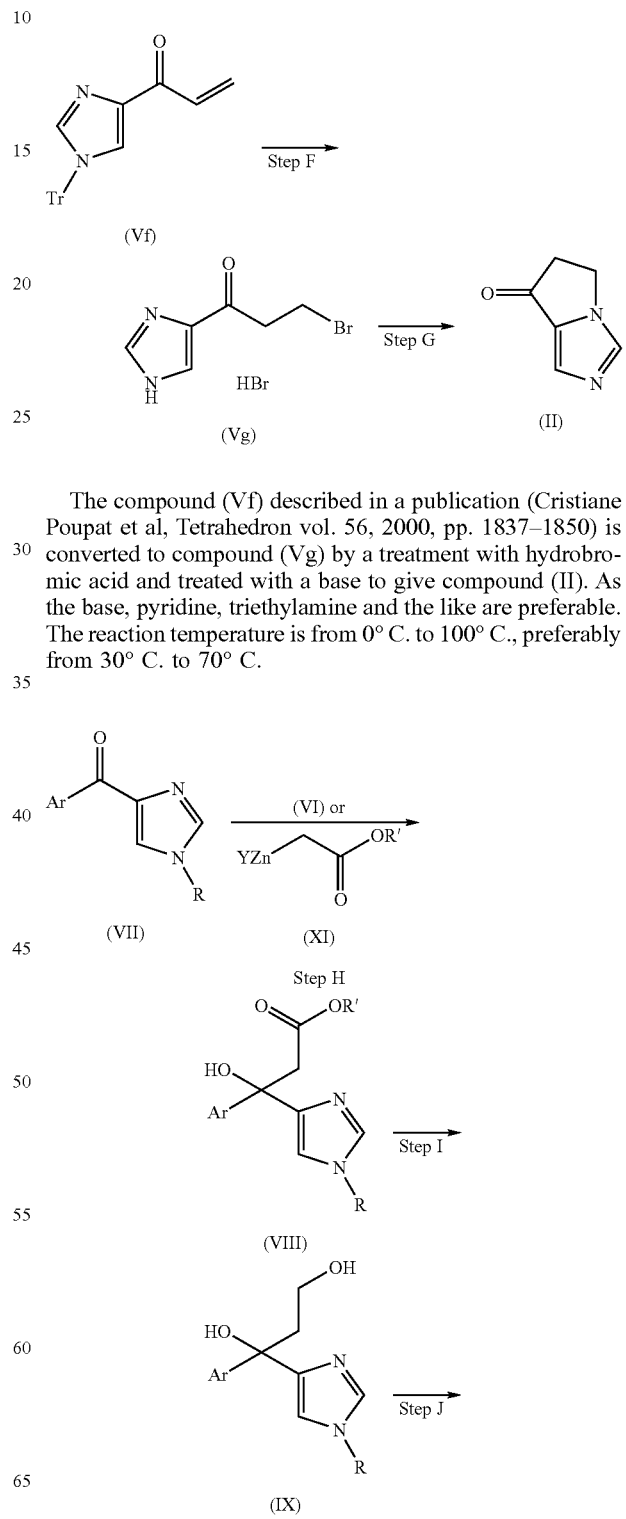

The compound (Vf) described in a publication (Cristiane Poupat et al, Tetrahedron vol. 56, 2000, pp. 1837–1850) is converted to compound (Vg) by a treatment with hydrobromic acid and treated with a base to give compound (II). As the base, pyridine, triethylamine and the like are preferable. The reaction temperature is from 0° C. to 100° C., preferably from 30° C. to 70° C.

wherein R is a protecting group (e.g., trityl group) and Q is a leaving group (e.g., methanesulfonyloxy group, p-toluenesulfonyloxy group etc.).

In step A, lithium salt (VI) obtained by treating ethyl acetate with lithium diisopropylamide is reacted with compound (Va) to give compound (Vb). The reaction temperature is from −80° C. to −40° C., preferably from −80° C. to -continued

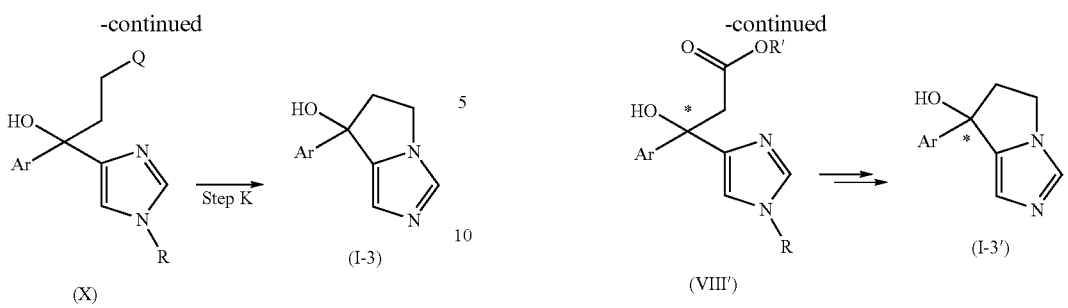

wherein Y is a halogen atom (iodine, bromine, chlorine), R' is a lower alkyl group having 1 to 6 carbon atoms (e.g., methyl, ethyl, propyl, isopropyl, t-butyl group etc.), arylalkyl group (e.g., benzyl group etc.), and other symbols are as defined above.

In Step H, compound (VII) is reacted with lithium salt (VI) or organic zinc compound (XI) to give compound (VIII). When lithium salt (VI) is reacted, the reaction temperature is from −80° C. to 0° C., preferably from −60° C. to −40° C. When compound (VII) is reacted with organic zinc compound (XI: Reformatsky reagent) to give compound (VIII), the reaction temperature is from −80° C. to 40° C., preferably from −40° C. to 10° C. The Reformatsky reagent can be prepared by a method described in a publication (Alois Fürstner, Angew. Chem. Int. Ed. Engl. 1993, vol. 32, pp. 164–189). By reducing the ester moiety of Compound (VIII), compound (IX) can be obtained. The reducing agent to be used for this reaction is exemplified by lithium aluminum hydride, sodium borohydride, sodium bis(2-methoxyethoxy)aluminum hydride [Red-Al™] and the like. The reaction temperature is from −40° C. to 30° C., preferably from 20° C. to 0° C. Moreover, by converting an alcohol moiety of compound (IX) to a leaving group such as methanesulfonate, halogen (bromine, chlorine etc.) and the like to give compound (X), and heating the resulting compound in the presence or absence of a base, compound (I-3) can be obtained. The base to be used for this cyclization reaction is preferably triethylamine, ethyldiisopropylamine and the like. The reaction temperature is 30° C.–120° C., preferably 50° C.–80° C. As the reaction solvent, toluene, acetonitrile, methanol, ethanol, a mixed solvent thereof and the like are preferable.

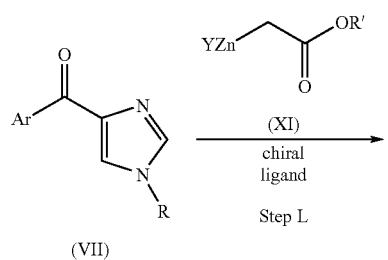

In step H, by reaction of compound (VII) and organic zinc compound (XI) in the presence of a suitable chiral ligand affords optically active compound (VIII'). As the chiral ligand, optically active amino alcohol derivative and optically active amine derivative are exemplified. Examples of the optically active amino alcohol derivative include cinchona alkaloid such as cinchonine, cinchonidine, quinidine, quinine etc., N-methylephedrine, norephedrine, 3-exo-(dimethylamino)isoborneol, 1-methyl-2-pyrrolidinemethanol, 1-benzyl-2-pyrrolidinemethanol, 2-[hydroxy(diphenyl)methyl]-1-methylpyrrolidine and the like. Examples of the optically active amine include spartein and the like. By using a suitable chiral ligand, compound (VIII') having a desired steric configuration can be obtained. The optically active compound (VIII') can be led to optically active compound (I-3') under the reaction conditions similar to those for conversion of compound (VIII) to compound (I-3).

The compound (VII), which is a starting material of the above-mentioned reaction, can be obtained according to the method described in WO99/54309. It is also possible to obtain by a single step for the reaction of compound (III') and compound (XII).

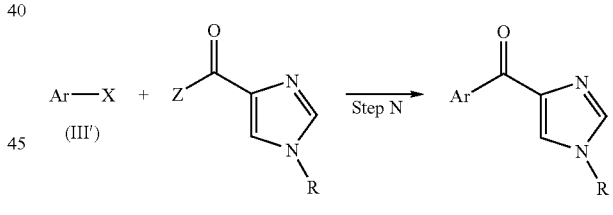

wherein Z is substituted amino group (e.g., dimethylamino, N-methyl-N-methoxyamino, morpholino, piperidino etc.) and other symbols are as defined above.

This reaction can be carried out under the same reaction conditions as in the reaction of compound (II) and compound (III').

The compound (I) can be efficiently resolved optically by the use of a chiral column (e.g., CHIRALPAK AD, Daicel Chemical Industries, Ltd.). Moreover, a diastereomeric salt with an optically active acid is produced and, utilizing difference in solubility, a desired optically active compound can be separated.

A method for preferably separating the optically active compound of the present invention, namely, the production method of an optically active compound of compound (I), particularly an optically active compound of the compound of the formula (I-1), is described in detail in the following. The present invention is characterized by the use of an optically active compound of the following the formula (IV) as an optical resolution reagent.

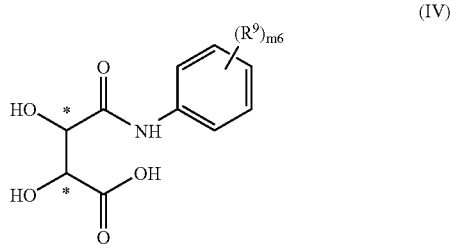

Particularly preferably, tartranilic acid of the formula (IV-1) is used.

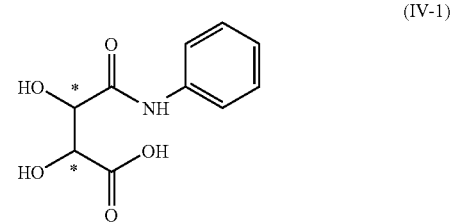

The following explains the case where tartranilic acid is used as an optical resolution reagent.

Both the (−)-compound and (+)-compound of a resolving agent, tartranilic acid, to be used in the present invention can be produced by a known method, for example, the method described in J. Am. Chem. Soc., 70, 1352 (1948), J. Org. Chem., 33, 3993 (1968), JP-A-10-218847, JP-A-2001-89431, or a method described in JP-A-10-218847. Both the (−)-tartranilic acid and (+)-tartranilic acid can be used as a resolving agent.

The optical resolution of an optical isomer mixture of the compound of the formula (I), particularly the compound of the formula (I-1), using an optically active tartranilic acid, can be performed by the following steps. An example compound to be recited later, 6-(7-hydroxy-6,7-dihydro-5H-pyrrolo[1,2-c]imidazol-7-yl)-N-methyl-2-naphthamide, is taken as an example of the compound of the formula (I), particularly the compound of the formula (I-1) for the following explanation. In the present invention, the optical isomer mixture encompasses not only a racemic mixture containing the same amounts of the (+)-compound and (−)-compound, but also a mixture containing one of the optical isomers in a greater amount than the other.

A diastereomeric salt is first formed in a suitable solvent from an optical isomer mixture of 6-(7-hydroxy-6,7-dihydro-5H-pyrrolo[1,2-c]imidazol-7-yl)-N-methyl-2-naphthamide and optically active tartranilic acid. The hardly soluble salt that precipitates here contains 6-(7-hydroxy-6,7-dihydro-5H-pyrrolo[1,2-c]imidazol-7-yl)-N-methyl-2-naphthamide and tartranilic acid in a molar ratio of 1:2.

When (−)-tartranilic acid is used as a resolving agent, a hardly soluble salt is formed with (+)-6-(7-hydroxy-6,7-dihydro-5H-pyrrolo[1,2-c]imidazol-7-yl)-N-methyl-2-naphthamide, which can be isolated as crystals. When (+)-tartranilic acid is used as a resolving agent, a hardly soluble salt with (−)-6(7-hydroxy-6,7-dihydro-5H-pyrrolo[1,2-c]imidazol-7-yl)-N-methyl-2-naphthamide precipitates, and (+)-6-(7-hydroxy-6,7-dihydro-5H-pyrrolo[1,2-c]imidazol-7-yl)-N-methyl-2-naphthamide can be isolated in a free form or in the form of a salt, from the mother liquor after removal of the precipitates.

The amount of use of the tartranilic acid relative to 6-(7-hydroxy-6,7-dihydro-5H-pyrrolo[1,2-c]imidazol-7-yl)-N-methyl-2-naphthamide is 0.1 to 4-fold moles, preferably 1 to 2-fold moles. It is also possible to concurrently use mineral acid, such as hydrochloric acid, sulfuric acid, phosphoric acid and the like, or organic acids, such as acetic acid, propionic acid, fumaric acid, maleic acid, and the like along with a resolving agent to achieve the molar ratio mentioned above.

The preferable solvent to be used dissolves 6-(7-hydroxy-6,7-dihydro-5H-pyrrolo[1,2-c]imidazol-7-yl)-N-methyl-2-naphthamide and tartranilic acid, does not cause chemical changes of these compounds, and makes one of the produced diastereomeric salts less soluble. For example, water, alcohols such as methanol, ethanol, 1-propanol, 2-propanol etc., ethers such as diethyl ether, diisopropyl ether, tert-butylmethyl ether, tetrahydrofuran, tetrahydropyran, 1,2-dimethoxyethane etc., ketones such as acetone, 2-butanone etc., nitriles such as acetonitrile etc., esters such as methyl acetate, ethyl acetate etc., hydrocarbons such as pentane, hexane etc., aromatic hydrocarbons such as toluene, xylene etc., and the like can be used solely or in combination. The amount of use thereof is generally 1 to 500-fold amount, preferably 1 to 200-fold amount, relative to 6-(7-hydroxy-6,7-dihydro-5H-pyrrolo[1,2-c]imidazol-7-yl)-N-methyl-2-naphthamide. The temperature is generally 15° C. or higher and may be any as long as it is below boiling point of the solvent used.

One of the salts can be crystallized by cooling or concentrating after forming diastereomeric salts. Depending on the conditions, a less soluble salt can be precipitated by only allowing to stand at room temperature, without a step of cooling or concentration.

The precipitated diastereomeric salt can be easily separated by a general solid-solution separation method, such as filtration, centrifugal separation and the like. The separated crystals of the diastereomeric salt can achieve a higher purity as necessary by a known method, such as recrystallization and the like. It is also possible to isolate an optically active compound in a free form or in the form of a salt, from the mother liquor after removal of the less soluble salt.

The salt thus obtained can be decomposed by any known method. For example, the salt is treated with alkali or acid in an aqueous solution to achieve the object. Generally, it is treated with an aqueous base, such as an aqueous sodium hydroxide solution, an aqueous sodium bicarbonate solution and the like, and the liberated optically active 6-(7-hydroxy-6,7-dihydro-5H-pyrrolo[1,2-c]imidazol-7-yl)-N-methyl-2-naphthamide is treated according to a solid-solution separation method, such as filtration and centrifugal separation, or extraction with an organic solvent and the like. The treatment with a base proceeds generally at a temperature of from −10° C. to about 25° C., and the amount of the base to be used is 1 to 5-fold moles relative to the salt. The concentration of the base is 1–50 wt %, preferably 1–20 wt %.

It is possible to recover the optically active tartranilic acid used as a resolving agent for recycled use by making the basic aqueous layer after separating 6-(7-hydroxy-6,7-dihydro-5H-pyrrolo[1,2-c]imidazol-7-yl)-N-methyl-2-naphthamide acidic with an acid, such as hydrochloric acid, sulfuric acid and the like.

In the same manner as in the above-mentioned method, the compound of the formula (I), particularly the compound of the formula (I-1), other than 6-(7-hydroxy-6,7-dihydro-5H-pyrrolo[1,2-c]imidazol-7-yl)-N-methyl-2-naphthamide, is treated with an optical resolution reagent of the formula (VI), such as tartranilic acid and the like, to give an optically active compound.

When the compound of the present invention is obtained in a free form, it may be converted to a salt by a conventional method, and when the compound is obtained as a salt, it may be converted to a free form or a different salt by a conventional method.

The compound thus obtained and optically active compounds thereof can be isolated and purified from a reaction mixture by a known method, such as phasic transfer, concentration, solvent extraction, fractional distillation, crystallization, recrystallization, chromatography and the like.

In the above-mentioned respective reactions, a protecting group may be used for amino group, carboxyl group and hydroxyl group of the compound or a salt thereof to be subjected to reaction but irrelevant to the reaction, wherein the protecting group can be added and removed by a known method.

As the protecting group of amino, there are exemplified formyl, and $C_{1-6}$ alkyl-carbonyl (e.g., acetyl, propionyl etc.), phenylcarbonyl, $C_{1-6}$ alkyloxy-carbonyl (e.g., methoxycarbonyl, ethoxycarbonyl etc.), phenyloxycarbonyl, $C_{7-10}$ aralkyloxy-carbonyl (e.g., phenyl-$C_{1-4}$ alkyloxy-carbonyl such as benzyloxycarbonyl etc.), trityl, phthaloyl, N,N-dimethylaminomethylene and the like, all of which are optionally substituted. Examples of these substituents include halogen atom (e.g., fluorine, chlorine, bromine, iodine etc.), formyl, $C_{1-6}$ alkyl-carbonyl (e.g., acetyl, propionyl, valeryl etc.), nitro group and the like, wherein the number of substituents is approximately 1 to 3.

As the protecting group of carboxyl group, there are exemplified $C_{1-6}$ alkyl (e.g., methyl, ethyl, propyl, isopropyl, butyl, tert-butyl etc.), phenyl, trityl, silyl and the like, all of which are optionally substituted. Examples of these substituents include halogen atom (e.g., fluorine, chlorine etc.), formyl, $C_{1-6}$ alkyl-carbonyl (e.g., acetyl, propionyl, valeryl etc.), nitro group and the like, wherein the number of substituents is approximately 1 to 3.

As the protecting group of hydroxyl group, there are exemplified $C_{1-6}$ alkyl (e.g., methyl, ethyl, propyl, isopropyl, butyl, tert-butyl etc.), phenyl, $C_{7-10}$ aralkyl (e.g., phenyl-$C_{1-4}$ alkyl such as benzyl etc.), formyl, $C_{1-6}$ alkyl-carbonyl (e.g., acetyl, propionyl etc.), phenyloxycarbonyl, benzoyl, ($C_{7-10}$ aralkyloxy)carbonyl (e.g., phenyl-$C_{1-4}$ alkyloxy-carbonyl such as benzyloxycarbonyl etc.), pyranyl, furanyl or silyl and the like, all of which are optionally substituted. Examples of these substituents include halogen atom (e.g., fluorine, chlorine etc.), $C_{1-6}$ alkyl (e.g., methyl, ethyl, propyl etc.), phenyl, $C_{7-10}$ aralkyl (e.g., phenyl-$C_{1-4}$ alkyl such as benzyl etc.), nitro group and the like, wherein the number of substituents is approximately 1 to 4.

For removing the protecting group, a method known per se or a method analogous thereto is used. For example, a method comprising treatment with an acid, a base, reduction, ultraviolet radiation, hydrazine, phenylhydrazine, sodium N-methyldithiocarbamate, tetrabutyl ammonium fluoride, palladium acetate and the like is used.

The compound (I) can be obtained as stable crystals by forming a salt with an acid. Such salt has higher solubility in water and has superior oral absorbability. As such acid, organic acids, such as fumaric acid, oxalic acid, malic acid and the like, are preferable, particularly preferably fumaric acid.

The compound (I) and a prodrug thereof (hereinafter the both are also referred to as the compound of the present invention) provide a superior effect as a medicine and show a particularly superior steroid $C_{17,20}$-lyase-inhibitory activity. The compound of the present invention shows low toxicity and lower side effects. Therefore, they can be used for mammals (e.g., human, calf, horse, pig, dog, cat, monkey, mouse, rat etc., particularly human), are useful as, for example, (i) an androgen or estrogen reducing agent or (ii) an agent for the treatment or prevention of various diseases such as diseases related to androgen or estrogen, such as (1) primary cancer, metastasis or recurrence of malignant tumor (e.g., prostate cancer, breast cancer, uterine cancer, ovarian cancer etc.), (2) various symptoms accompanying the cancers (e.g., pain, cachexia etc.), and (3) prostatic hypertrophy, masculinism, hypertrichosis, male pattern baldness, male infant-type prematurity, endometriosis, hysteromyoma, adenomyosis of uterus, mastopathy, polycystic ovary syndrome and the like.

In the specification, the androgen or estrogen reducing agent means a medicine that suppresses formation of androgen and the subsequent formation of estrogen (estrogen is synthesized from androgen as a substrate).

The compound of the present invention shows a superior effect even when used alone. When combined with a different pharmaceutical preparation or therapy, the effect can be reinforced furthermore. As the combination drug and therapy, for example, there are mentioned, but not limited to, "sex hormone agents (hormone preparation)", "alkylating agents", "antimetabolites", "carcinostatic antibiotics", "plant alkaloids", "immunotherapeutic agents", "pharmaceutical agents inhibiting action of cell growth factor and its receptor" and the like (hereinafter to be briefly referred to as a combination drug). Besides the combined use, the compound of the present invention and a different compound that provides preferable efficacy (specifically, various efficacy to be mentioned below) when combined with the compound may be contained in a single preparation to give a mixture.

Examples of the "hormone preparation" include fosfestrol, diethylstilbestrol, chlorotrianisene, medroxyprogesterone acetate, megesterol acetate, chlormadinone acetate, cyproterone acetate, danazol, allylestrenol, gestrinone, mepartricine, raloxifene, ormeloxifene, levormeloxifene, antiestrogen (e.g., tamoxifen citrate, toremifene citrate etc.), contraceptive pill, mepitiostane, testolactone, aminoglutethimide, LHRH receptor modulator [LH-RH receptor agonist (e.g., goserelin acetate, buserelin acetate, leuprorelin acetate etc.), LH-RH receptor antagonist (e.g., ganirelix, cetrorelix, abarelix etc.)], droloxifene, epitiostanol, ethinylestradiol sulfonate, aromatase inhibitor (e.g., fadrozole hydrochloride, anastrozole, letrozole, exemestane, vorozole, formestane etc.), antiandrogen (e.g., flutamide, bicalutamide, nilutamide etc.), 5α-reductase inhibitor (e.g., finasteride, episteride etc.), adrenocortical hormone preparation (e.g., cortisol, dexamethasone, prednisolone, betamethasone, triamcinolone etc.), androgen synthesis inhibitor (e.g., abiraterone etc.), retinoid and an agent to delay metabolism of retinoid (e.g., liarozole etc.) and the like.

Examples of the "alkylating agents" include nitrogen mustard, nitrogen mustard-n-oxide hydrochloride, chrorambucil, cyclophosphamide, ifosfamide, thiotepa, carboquone, improsulfan tosilate, busulfan, nimustine hydrochloride, mitobronitol, melphalan, dacarbazine, ranimustine, estramustine phosphate sodium, triethylene melamine, carmustine, lomustine, streptozocin, pipobroman, etoglucide, carboplatin, cisplatin, miboplatin, nedaplatin, oxaliplatin, altretamin, ambamustine, dibrospidium hydrochloride, fotemustine, prednimustine, pumitepa, ribomustin, temozolomide, treosulfan, trophosphamide, zinostatin stimalamer, adozelesin, cystemstin, bizelesin and the like.

Examples of the "antimetabolites" include mercaptopurine, 6-mercaptopurine riboside, thioinosine, methotrexate, enocitabine, cytarabine, cytarabine ocphosphate, ancitabine hydrochloride, 5-FU pharmaceutical agents (e.g., fluorouracil, tegafur, UFT, doxifluridine, carmofur, galocitabine, emitefur etc.), aminopterin, calcium leucovorin, tabloid, butocin, calcium folinate, calcium levofolinate, cladribine, fludarabine, gemcitabine, hydroxycarbamide, pentostatin, piritrexim, idoxuridine, mitoguazone, tiazofurin and the like.

Examples of the "carcinostatic antibiotics" include actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride and the like.

Examples of the "plant alkaloids" include etoposide, toposide phosphate, vinblastine sulfate, vincristine sulfate, indesine sulfate, teniposide, paclitaxel, vinorelbine and the like.

Examples of the "immunotherapeutic agents" (BRM) include picibanil, krestin, sizofiran, lentinan, ubenimex, interferon, interleukin, macrophage colony stimulating factor, granulocyte-colony stimulating factor, erythropoietin, lymphotoxin, BCG vaccine, *Corynebacterium parvum*, levamisole, polysaccharide K, procodazol and the like.

As the "cell growth factor" in the "pharmaceutical agents inhibiting action of the cell growth factor and its receptor", any substance can be used as long as it enhances proliferation of cells. In general, a factor which is a peptide having a molecular weight of not more than 20,000, and which can show effect upon binding with receptor at a low concentration is exemplified. Specific examples include (1) EGF (epidermal growth factor) or a substance having substantially the same activity therewith [e.g., EGF, heregulin ($HER^2$ ligand) etc.], (2) insulin or a substance having substantially the same activity therewith [e.g., insulin, IGF (insulin-like growth factor)-1, IGF-2 etc.], (3) FGF (fibroblast growth factor) or a substance having substantially the same activity therewith [e.g., acidic FGF, basic FGF, KGF (keratinocyte growth factor), FGF-10 etc.], (4) other cell growth factors [e.g., CSF (colony stimulating factor), EPO (erythropoietin), IL-2(interleukin-2), NGF (nerve growth factor), PDGF (platelet-derived growth factor), TGFβ (transforming growth factor β), HGF (hepatocyte growth factor), VEGF (vascular endothelial growth factor) etc.] and the like.

The "receptor of the cell growth factor" may be any receptor as long as it has a binding ability with the above-mentioned cell growth factor. Specific examples include EGF receptor, $HER^2$ (heregulin receptor), insulin receptor, IGF receptor, FGF receptor-1, FGF receptor-2 and the like.

Examples of the "pharmaceutical agents inhibiting action of the cell growth factor" include antibodies against cell growth factor and receptor thereof, such as EGF receptor antibody (e.g., cetuximab) and HER2 antibody (e.g., herceptin); tyrosine kinase inhibitors such as Iressa (EGF receptor tyrosine kinase inhibitor), TAK-165 (HER2 tyrosine kinase inhibitor), GW2016 (EGF receptor/HER2 tyrosine kinase inhibitor) and the like; ribozyme that inhibits expression of cell growth factor and receptor thereof; antisense medicaments and the like.

In addition to the aforementioned pharmaceutical agents, L-asparaginase, aceglatone, procarbazine hydrochloride, cobalt protoporphyrin-complex, mercurial hematoporphyrin-sodium, topoisomerase I inhibitor (e.g., irinotecan, topotecan etc.), topoisomerase II inhibitor (e.g., sobuzoxane etc.), differentiation inducing agent (e.g., retinoid, vitamine D etc.), angiogenesis inhibitor, α-blocker (e.g., tamsulosin hydrochloride etc.) and the like can be also used.

Along with a chemical therapy to administer the compound of the present invention, for example, a therapy other than the chemical therapy such as an operation including orchiectomy, thermotherapy, radiation therapy and the like can be applied in combination.

Particularly, the compound of the present invention can more effectively remove androgen or estrogen in blood when used in combination with an LHRH receptor modulator (LHRH modulator) such as LHRH receptor agonist (e.g., goserelin acetate, buserelin acetate, leuprorelin acetate etc.) and LHRH receptor antagonist (e.g., ganirelix, cetrorelix, abarelix etc.).

The compound of the present invention has high selectivity to steroid $C_{17,20}$-lyase and shows less influence on drug metabolizing enzyme, such as CYP3A4. Therefore, it serves well as a safe pharmaceutical agent with less limitation on combined drug.

For combined use of compound (I) and combination drug, the administration time of compound (I) and combination drug is not limited, and compound (I) and combination drug may be simultaneously administered to the administration objects or administered with time lag. The dose of the combination drug may be similar to that clinically employed, which can be determined as appropriate depending on the administration objects, administration route, disease, combination and the like.

The mode of administration of compound (I) and combination drug is not particularly limited, and compound (I) and combination drug only need to be combined on administration. Such administration mode is exemplified by (1) administration of a single pharmaceutical preparation obtained by simultaneous formulation of compound (I) and combination drug, (2) simultaneous administration of two kinds of pharmaceutical preparations obtained by separate formulation of compound (I) and combination drug by the same administration route, (3) time lag administration of two kinds of pharmaceutical preparations obtained by separate formulation of compound (I) and combination drug by the same administration route, (4) simultaneous administration of two kinds of pharmaceutical preparations obtained by separate formulation of compound (I) and combination drug by different administration routes, (5) time lag administration of two kinds of pharmaceutical preparations obtained by separate formulation of compound (I) and combination drug by different administration routes (e.g., administration of compound (I)→combination drug and administration in reverse order) and the like.

As the pharmaceutically acceptable carrier to be used in the present invention, various organic and inorganic carrier substances for conventional production material are used and appropriately added as an excipient, a lubricant, a binder, a disintegrating agent and a thickener to solid preparations; as a solvent, a dispersing agent, a solubilizer, a suspending agent, an isotonicity agent, a buffer and a soothing agent to liquid preparations, and the like. Where necessary, additives such as an antiseptic, an antioxidant, a coloring agent, a sweetener and the like can be used according to a conventional method. Preferable examples of the excipient include lactose, sucrose, D-mannitol, starch, crystalline cellulose, light anhydrous silicic acid and the like. Preferable examples of the lubricant include magnesium stearate, calcium stearate, talc, colloidal silica and the like. Preferable examples of the binder include crystalline cellulose, sucrose, D-mannitol, dextrin, hydroxypropylcellulose, hydroxypropylmethylcellulose, polyvinylpyrrolidone and the like. Preferable examples of the disintegrating agent include starch, carboxymethyl cellulose, carboxymethyl cellulose calcium, crosscarmellose sodium, sodium carboxymethyl starch and the like. Preferable examples of the thickener include natural gums, cellulose derivative, acrylate polymer and the like. Preferable examples of the solvent include water for injection, alcohol, propylene glycol, Macrogol, sesame oil, corn oil and the like. Preferable examples of the dispersing agent include Tween 80, HCO 60, polyethylene glycol, carboxymethyl cellulose, alginate sodium and the like. Preferable examples of the solubilizer include polyethylene glycol, propylene glycol, D-mannitol, benzyl benzoate, ethanol, tris-aminomethane, cholesterol, triethanolamine, sodium carbonate, sodium citrate and the like. Preferable examples of the suspending agent include surfactants such as stearyl triethanolamine, sodium lauryl sulfate, lauryl aminopropionate, lecithin, benzalkonium chloride, benzethonium chloride, glyceryl monostearate and the like; hydrophilic polymers such as polyvinyl alcohol, polyvinylpyrrolidone, carboxymethylcellulose sodium, methylcellulose, hydroxymethylcellulose, hydroxyethyl cellulose, hydroxypropylcellulose etc., and the like. Preferable examples of the isotonicity agent include sodium chloride, glycerine, D-mannitol and the like. Preferable examples of the buffer include buffer solutions of phosphate, acetate, carbonate, citrate and the like. Preferable examples of the soothing agent include benzyl alcohol and the like. Preferable examples of the antiseptic include p-hydroxybenzoic acid esters, chlorobutanol, benzyl alcohol, phenethyl alcohol, dehydroacetic acid, sorbic acid and the like. Preferable examples of the antioxidant include sulfite, ascorbic acid and the like.

The pharmaceutical preparation of the present invention can be produced according to a conventional method, wherein the content of the compound of the present invention in the preparation is generally 0.1–100% (w/w). Specific examples are shown in the following.

(1) Tablet, Powder, Granule, Capsule:

These can be produced by adding, for example, an excipient, a disintegrating agent, a binder, a lubricant and the like to the compound of the present invention, and subjecting the mixture to compression molding, and where necessary, coating for masking of taste, enteric coating or coating for sustention.

(2) Injection:

An injection can be produced by preparing the compound of the present invention into an aqueous injection together with, for example, a dispersing agent, a preservative, an isotonicity agent and the like, or dissolving, suspending or emulsifying in vegetable oil, such as olive oil, sesame oil, cottonseed oil, corn oil etc., propylene glycol and the like, to give an oily injection.

(3) Suppository:

A suppository can be produced by making the compound of the present invention into an oily or aqueous solid, semisolid or liquid composition. Examples of the oily base to be used for such a composition include glyceride of higher fatty acid (e.g., cacao butter, Witepsol etc.), medium fatty acid (e.g., migliol etc.), vegetable oil (e.g., sesame oil, soybean oil, cottonseed oil etc.) and the like. Examples of the aqueous gel base include natural gums, cellulose derivative, vinyl polymer, acrylate polymer and the like.

While the content of the compound of the present invention in these preparations varies depending on the kind of preparation, it is generally 0.01–50%.

The amount of use of the compound of the present invention in the aforementioned pharmaceutical preparation varies depending on the compound to be selected, animal species selected to be the administration object, frequency of administration and the like, and the compound exerts effectiveness over a wide range. For example, the daily dose of a pharmaceutical preparation of the present invention, when orally administered to an adult patient with solid tumor (e.g., patient with prostate cancer) as expressed in the effective amount of the compound of the present invention, is generally about 0.001 to about 500 mg/kg body weight, preferably about 0.1 to about 40 mg/kg body weight, more preferably about 0.5 to about 20 mg/kg body weight. When it is used for parenteral administration in combination with a different anticancer agent, the dose is generally smaller than the doses mentioned above. However, the amount of the compound actually administered is determined based on the selection of the compound, various dosage forms, age, body weight and sex of the patient, level of disease state, administration route, the period and intervals of the administration and the like, and can be modified at any time according to the judgment of doctors.

While the administration route of the aforementioned pharmaceutical preparation is not particularly limited by various conditions, for example, it can be administered orally or parenterally. As used herein, by the "parenteral" is meant intravenous, intramuscular, subcutaneous, intranasal, intracutaneous, instillation, intracranial, endorectal, intravaginal and intraperitoneal administrations.

The period and intervals of the administration of the aforementioned pharmaceutical preparation are modified according to various conditions and determined according to the judgment of doctors at any time. The administration method includes, for example, divisional administration, consecutive daily administration, intermittent administration, administration in large amounts in a short term, repeat administration and the like. In the case of oral administration, for example, the preparation is desirably administered once a day to several times a day (particularly 2 or 3 times a day) by dividing the dose. It is also possible to administer as a sustained release preparation or intravenous infusion over a long time.

The present invention is explained in more detail by way of the following Examples, Preparation Examples and Experimental Examples. These Examples are mere embodiments and do not limit the present invention in any way and can be modified as long as they do not deviate from the scope of the present invention.

EXAMPLES

Nuclear magnetic resonance spectrum ($^1$H-NMR) was measured in JEOL Ltd. JMTCO400/54 (400 MHz) (or Varian Gemini-200 (200 MHz)) using tetramethylsilane as the internal standard. The δ values are shown in ppm. The symbols in the Examples and Reference Examples mean the following and abbreviations in the Examples mean the following.

s: singlet, d: doublet, t: triplet, q: qualtet, dd: double doublet, dt: double triplet, dq: double qualtet, m: multiplet, br: broad, J: coupling constant, room temperature (r.t.): 0–30° C., DMF: dimethylformamide, THF: tetrahydrofuran.

Enantiomer excess (% ee) and diastereomer excess (% de) were measured by high performance liquid chromatography using an optical isomer separate column.

((High Performance Liquid Chromatography Conditions))
  column; CHIRALPAK AD, Daicel Chemical Industries, Ltd.
  mobile phase; hexane/ethanol 50/50
  flow rate; 0.5 ml/min.
  detection; UV 254 nm
  temperature; r.t.

Reference Example 1

Production of 6-bromo-N-methyl-2-naphthamide

6-Bromo-2-naphthoic acid (60.26 g), 1-ethyl-3-(3-dimethylaminopropyl)carbodiimide hydrochloride (55.21 g) and 1-hydroxy-1H-benzotriazole monohydrate (44.1 g) were dissolved in dimethylformamide (960 ml) under an argon atmosphere. N-Ethyldiisopropylamine (37.23 g) was added with stirring under ice-cooling. A solution (2M; 192 ml) of methylamine in THF was added and the mixture was stirred at room temperature for 18 h. The reaction mixture was poured into water (8 L) with stirring and the precipitate was collected by filtration. The precipitate was washed successively with water and diisopropyl ether, and dried in the presence of phosphorus pentaoxide at 70° C. to give the title compound (60.6 g) as a crystalline powder.

$^1$H-NMR(CDCl$_3$+CD$_3$OD) δ: 3.04 (3H, s), 7.60 (1H, dd, J=1.8 Hz, 8.6 Hz), 7.78 (2H, d, J=8.6 Hz), 7.85 (1H, dd, J=1.8 Hz, 8.6 Hz), 8.03 (1H, d, J=1.8 Hz), 8.25 (1H, s).

IR(KBr):3274, 1638, 1622, 1559, 1495, 1408, 1316, 1159 cm$^{-1}$.

Reference Example 2

Production of 6-bromo-N-cyclopropyl-2-naphthamide

6-Bromo-2-naphthoic acid (1.01 g), 1-ethyl-3-(3-dimethylaminopropyl)carbodiimide hydrochloride (0.92 g) and 1-hydroxy-1H-benzotriazole monohydrate (0.735 g; HOBt) were dissolved in dimethylformamide (16 ml) under an argon atmosphere. N-Ethyldiisopropylamine (0.62 g) was added with stirring under ice-cooling. Cyclopropylamine (0.37 g) was added and the mixture was stood with stirring at room temperature for 18 h. The reaction mixture was poured into ethyl acetate (0.15 L) and the mixture was washed successively with water and saturated brine. The mixture was dried over anhydrous sodium sulfate and the solvent was concentrated. The precipitated crystals were collected by filtration and dried to give the title compound (0.817 g) as colorless needle crystals.

$^1$H-NMR(CDCl$_3$) δ: 0.64–0.73 (2H, m), 0.87–0.97 (2H, m), 2.90–3.02 (1H, m), 6.42 (1H, br s), 7.60 (1H, dd, J=2.0 Hz, 8.8 Hz), 7.77 (2H, d, J=8.8 Hz), 7.82 (1H, dd, J=2.0 Hz, 8.8 Hz), 8.03 (1H, d, J=2.0 Hz), 8.21 (1H, d, J=2.0 Hz).

IR(KBr): 3254, 3061, 1632, 1618, 1541, 1491, 1318, 1138 cm$^{-1}$.

Reference Example 3

Production of 6-bromo-N-cyclobutyl-2-naphthamide

By reactions similar to those in Reference Example 2, using 6-bromo-2-naphthoic acid (1.01 g), 1-ethyl-3-(3-dimethylaminopropyl)carbodiimide hydrochloride (0.92 g), 1-hydroxy-1H-benzotriazole monohydrate (0.735 g; HOBt), dimethylformamide (16 ml), N-ethyldiisopropylamine (0.62 g) and cyclobutylamine (0.45 g), the title compound (0.89 g) was obtained as colorless needle crystals.

$^1$H-NMR(CDCl$_3$) δ: 1.72–1.88 (2H, m), 1.90–2.15 (2H, m), 2.40–2.57 (2H, m), 4.56–4.76 (1H, m), 6.43 (1H, d, J=7.6 Hz), 7.60 (1H, dd, J=1.8 Hz, 8.8 Hz), 7.77 (2H, d, J=8.8 Hz), 7.84 (1H, dd, J=1.8 Hz, 8.8 Hz), 8.02 (1H, s), 8.23 (1H, s).

IR(KBr): 3264, 2976, 1634, 1620, 1557, 1491, 1319, 1186 cm$^{-1}$.

Reference Example 4

Production of 6-bromo-N-isopropyl-2-naphthamide

By reactions similar to those in Reference Example 2 using 6-bromo-2-naphthoic acid (1.01 g), 1-ethyl-3-(3-dimethylaminopropyl)carbodiimide hydrochloride (0.92 g), 1-hydroxy-1H-benzotriazole monohydrate (0.735 g), dimethylformamide (16 ml), N-ethyldiisopropylamine (0.62 g) and isopropylamine (0.38 g), the title compound (0.80 g) was obtained as colorless needle crystals.

$^1$H-NMR(CDCl$_3$) δ: 1.31 (6H, d, J=6.6 Hz), 4.27–4.44 (1H, m), 6.09 (1H, d, J=7.8 Hz), 7.60 (1H, dd, J=1.8 Hz, 8.8 Hz), 7.78 (2H, d, J=8.8 Hz), 7.84 (1H, dd, J=1.8 Hz, 8.8 Hz), 8.03 (1H, d, J=1.8 Hz), 8.22 (1H, s).

IR(KBr): 3262, 2973, 1634, 1620, 1557, 1468, 1352, 1186 cm$^{-1}$.

Reference Example 5

Production of 6-bromo-N-ethyl-2-naphthamide

By reactions similar to those in Reference Example 2 using 6-bromo-2-naphthoic acid (1.01 g), 1-ethyl-3-(3-dimethylaminopropyl)carbodiimide hydrochloride (0.92 g), 1-hydroxy-1H-benzotriazole monohydrate (0.735 g), dimethylformamide (16 ml), N-ethyldiisopropylamine (1.45 g) and ethylamine hydrochloride (0.52 g), the title compound (0.67 g) was obtained as colorless needle crystals.

$^1$H-NMR(CDCl$_3$) δ: 1.30 (3H, t, J=7.3 Hz), 3.56 (2H, dq, J=5.6 Hz, 7.3 Hz), 6.29 (1H, br s), 7.60 (1H, dd, J=2.0 Hz, 8.8 Hz), 7.77 (2H, d, J=8.8 Hz), 7.85 (1H, dd, J=2.0 Hz, 8.8 Hz), 8.03 (1H, d, J=2.0 Hz), 8.24 (1H, s).

IR(KBr): 3275, 2976, 1638, 1620, 1555, 1460, 1314, 1186 cm$^{-1}$.

Reference Example 6

Production of ethyl 3-hydroxy-3-(1-trityl-1H-imidazol-4-yl)propanoate

Diisopropylamine (33.8 ml) was dissolved in dry THF (445 ml) under an argon atmosphere. A solution (1.6 M; 150 ml) of n-butyl lithium in hexane was added at not more than 0° C. with stirring under ice-cooling (ice-salt), and the mixture was stirred for 30 min. The mixture was then cooled to −70° C. in a dry ice-acetone bath and ethyl acetate (23.5 ml)/dry THF (60 ml) solution was added at not more than −65° C. The mixture was stood with stirring for 1 h 20 min. The reaction mixture was added to a solution (1185 ml) cooled to −70° C. of 1-trityl-4-formyl-1H-imidazole (67.7 g) in dry THF at not more than −60° C., and the mixture was stirred for 1 h. A 20% aqueous ammonium chloride solution (445 ml) was added to stop the reaction and the mixture was allowed to warm to room temperature over 1 h. An equivalent amount of water was added and the mixture was partitioned. The aqueous layer was extracted with ethyl acetate. The organic layer was combined and the mixture was dried over anhydrous sodium sulfate. The solvent was evaporated, and the precipitated crystals were finely divided with hexane, collected by filtration and dried to give the title compound (77.26 g) as colorless crystals.

$^1$H-NMR(CDCl$_3$) δ: 1.23 (3H, t, J=7.2 Hz), 2.85 (1H, d, J=7.2 Hz), 2.86 (1H, d, J=5.4 Hz), 3.51 (1H, d, J=5.2 Hz), 4.14 (2H, q, J=7.2 Hz), 5.11 (1H, q, J=5.6 Hz), 6.79 (1H, s), 7.06–7.17 (6H, m), 7.29–7.38 (9H, m), 7.39 (1H, s).

IR(KBr): 3152, 1725, 1597, 1493, 1445, 1368, 1277, 1127 cm$^{-1}$.

Reference Example 7

Production of 1-(1-trityl-1H-imidazol-4-yl)-1,3-propanediol

Lithium aluminum hydride (8.78 g) was suspended in dry THF (500 ml) under an argon atmosphere, and ethyl 3-hydroxy-3-(1-trityl-1H-imidazol-4-yl)propanoate (76 g)/dry THF (350 ml) solution was added at the same temperature with stirring under ice-cooling (ice-salt). The mixture was allowed to assume room temperature and stood with stirring for 2 h. The mixture was ice-cooled again and water/THF (1/6; 58.4 ml) was added to stop the reaction. An aqueous Rochelle salt solution (240 g/1.5 L) was added and the mixture was stood with stirring for 18 h. The organic layer was separated, washed with saturated brine and dried over anhydrous sodium sulfate. The solvent was evaporated and the residue was recrystallized from ethyl acetate-ether to give the title compound (58.8 g) as a colorless crystalline powder.

$^1$H-NMR(CDCl$_3$+CD$_3$OD) δ: 1.95–2.04 (2H, m), 3.79 (2H, t, J=5.6 Hz), 4.85 (1H, t, J=6.2 Hz), 6.78 (1H, s), 7.07–7.17 (6H, m), 7.28–7.38 (9H, m), 7.40 (1H, s).

IR(KBr): 3500–3000, 1597, 1491, 1445, 1343, 1130, 1053 cm$^{-1}$.

Reference Example 8

Production of 3-hydroxy-1-(1-trityl-1H-imidazol-4-yl)-1-propanone 1-(1-Trityl-1H-imidazol-4-yl)-1,3-propanediol (135.9 g) was dissolved in dichloromethane (1.76 L) and manganese dioxide (262 g) was added, which was followed by vigorous stirring at room temperature for 66 h. An insoluble material was filtered off by celite filtration and the filtrate was concentrated to dryness. The residue was suspended in ethyl acetate (1.5 L) and an aqueous solution (1 M; 3.5 L) of Rochelle salt was added, which was followed by stirring with a mechanical stirrer for 3 days. The reaction mixture was partitioned, and the organic layer was washed with saturated brine and dried over anhydrous sodium sulfate. The aqueous layer was extracted again with ethyl acetate and treated in the same manner. The organic layer was combined and the solvent was evaporated to give the title compound (129.3 g) as a pale-brown caramel.

$^1$H-NMR(CDCl$_3$) δ: 3.20 (2H, t, J=5.3 Hz), 3.67 (1H, t, J=6.0 Hz), 3.93–4.05 (2H, m), 7.06–7.17 (6H, m), 7.33–7.42 (9H, m), 7.46 (1H, d, J=1.4 Hz), 7.62 (1H, d, J=1.4 Hz).

IR(KBr): 3059, 1674, 1597, 1532, 1493, 1447, 1300, 1136 cm$^{-1}$.

Reference Example 9

Production of 5,6-dihydro-7H-pyrrolo[1,2-c]imidazol-7-one

3-Hydroxy-1-(1-trityl-1H-imidazol-4-yl)-1-propanone (129 g) was dissolved in ethyl acetate (2 L). While stirring under ice-cooling (ice-salt), triethylamine (65.8 ml) was added and then a solution of methanesulfonyl chloride (34.2 ml) in ethyl acetate (50 ml) was added. The mixture was stirred at the same temperature for 1 h and ice water (0.8 L) was added to the reaction mixture, which was followed by partitioning. The organic layer was washed with water and saturated brine, and dried over anhydrous magnesium sulfate. The solvent was evaporated under reduced pressure. The residue was dissolved in acetonitrile (2.36 L) and the mixture was stirred at 70° C. for 3 h. The reaction mixture was allowed to assume room temperature. Methanol (0.8 L) and triethylamine (61 ml) were added and the mixture was stirred again at 70° C. for 1.5 h. The solvent was evaporated under reduced pressure and ethyl acetate (200 ml) was added to the resulting residue. The insoluble material was filtered off. The solvent was evaporated and the residue was purified by silica gel column chromatography (eluent; methanol/ethyl acetate; 1/24–1/9). The eluate was recrystallized from methanol/ethyl acetate to give the title compound (18.84 g) as pale brown crystals.

$^1$H-NMR(CDCl$_3$) δ: 3.24 (2H, t, J=6.5 Hz), 4.41 (2H, t, J=6.5 Hz), 7.60 (1H, s), 7.74 (1H, s).

IR(KBr): 3121, 1713, 1537, 1489, 1412, 1319, 1204, 1109 cm$^{-1}$.

Reference Example 10

Production of 3-bromo-4'-fluoro-1,1'-biphenyl

A suspension of 1,3-dibromobenzene (25.3 g), 4-fluorophenylboronic acid (5.00 g) and 2M aqueous sodium carbonate solution (35.7 ml) in DMF (250 ml) was degassed. Tetrakis(triphenylphosphine)palladium(0) (2.06 g) was added under an argon atmosphere and the mixture was refluxed under heating for 21 h. Water was added to the reaction mixture and the mixture was extracted with ethyl acetate, washed twice with water and washed with saturated brine, and dried over anhydrous magnesium sulfate. The solvent was evaporated under reduced pressure and distilled under reduced pressure to give the title compound (5.84 g) as a colorless oil.

$^1$H-NMR (CDCl$_3$) δ: 7.09–7.18 (2H, m), 7.31 (1H, d, J=7.8 Hz), 7.44–7.55 (4H, m), 7.67–7.69 (1H, m).

IR (KBr): 1607, 1563, 1514, 1472, 1235, 1159, 835, 829, 781 cm$^{-1}$.

Reference Example 11

Production of 6-(6,7-dihydro-5H-pyrrolo[1,2-c]imidazol-7-yl)-N-methyl-2-naphthamide

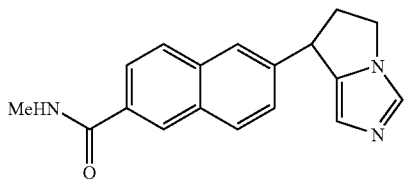

6-(7-Hydroxy-6,7-dihydro-5H-pyrrolo[1,2-c]imidazol-7-yl)-N-methyl-2-naphthamide (77 mg) was dissolved in methanol (5 ml). 1 N Hydrochloric acid (0.5 ml) and 10% palladium carbon (50% wet, 39 mg) were added, and the mixture was vigorously stirred for 12 h under 4 kg/cm$^2$ hydrogen atmosphere. The catalyst was filtered off and the residue was washed with methanol. The filtrate and the washing were combined and aqueous potassium carbonate solution (0.25 M; 1 ml) was added. After neutralization, the solvent was evaporated under reduced pressure, and the residue was purified by flash silica gel column chromatography (eluent, chloroform/methanol containing ammonia (7%); 19/1). The eluate was recrystallized from chloroform-ether to give the title compound (53 mg) as colorless crystals.

$^1$H-NMR(CDCl$_3$) δ: 2.55–2.74 (1H, m), 3.07 (3H, d, J=5.0 Hz), 3.04–3.26 (1H, m), 4.01–4.27 (2H, m), 4.57 (1H, t, J=7.6 Hz), 6.62 (1H, q, J=5.0 Hz), 6.79 (1H, s), 7.39 (1H, dd, J=1.6 Hz, 8.4 Hz), 7.55 (1H, s), 7.70 (1H, s), 7.77–7.95 (3H, m), 8.29 (1H, s).

IR(KBr): 3210, 1644, 1605, 1553, 1489, 1410, 1321 cm$^{-1}$.

Reference Example 12

Production of 5,6-dihydro-7H-pyrrolo[1,2-c]imidazol-7-one (i) Production of 3-bromo-1-(1H-imidazol-4-yl)-1-propanone 1-(1-Trityl-1H-imidazol-4-yl)-2-propen-1-one (29.0 g) was dissolved in acetic acid (130 ml) and the mixture was cooled to 10° C. A 25% solution of hydrogen bromide in acetic acid (100 ml) was added and the mixture was stirred at room temperature for 2 h. Isopropyl ether was added to the reaction mixture and the precipitated crystals were collected by filtration and washed with diisopropyl ether to give the title compound (22.3 g) as a pale yellow powder.

$^1$H-NMR (CD$_3$OD) δ: 3.54–3.81 (4H, m), 8.50 (1H, d, J=1.2 Hz), 9.15 (1H, d, J=1.2 Hz).

(ii) Production of 5,6-dihydro-7H-pyrrolo[1,2-c]imidazol-7-one

3-Bromo-1-(1H-imidazol-4-yl)-1-propanone (28.5 g) was suspended in acetonitrile (1100 ml) and the suspension was warmed to 70° C. A solution of triethylamine (15.3 ml) in acetonitrile (25 ml) was slowly added dropwise and the mixture was stirred at 70° C. for 2 h. Triethylamine (25 ml) was further added and the mixture was stirred for 30 min. The reaction mixture was cooled to room temperature and the insoluble material was filtered off. The solvent was evaporated and the residue was dissolved in ethyl acetate again. The insoluble material was filtered off and the solvent was evaporated. The resulting residue was subjected to silica gel column chromatography (eluent; dichloromethane:methanol containing ammonia (5%)=10:1) for purification to give the title compound (6.67 g) as a colorless powder.

Reference Example 13

Production of N,N-diisopropyl-6-[(1-trityl-1H-imidazol-4-yl)carbonyl]-2-naphthamide (i) Production of 6-bromo-N,N-diisopropyl-2-naphthamide A suspension of 6-bromo-2-naphthoic acid (100 g), thionyl chloride (37.7 ml) and DMF (0.5 ml) in THF (1000 ml) was stirred at 60° C. with heating for 90 min. After cooling to room temperature, the solvent was evaporated under reduced pressure. The resulting solid was dissolved in toluene and the solvent was evaporated to give 6-bromo-2-naphthoyl chloride as a pale yellow powder.

This was dissolved in anhydrous THF (400 ml) and the mixture was added dropwise to a solution of diisopropylamine (112 ml) and triethylamine (112 ml) in THF (800 ml) under ice-cooling. The mixture was stirred at room temperature for 1 h and a half amount of the solvent was evaporated under reduced pressure. The residue was diluted with ethyl acetate and washed successively with water, 1 N aqueous sodium hydroxide solution, water and saturated brine. After drying over magnesium sulfate, the solvent was evaporated and the obtained solid was washed with isopropyl ether to give the title compound (117 g) as a colorless scale.

$^1$H-NMR (CDCl$_3$) δ: 1.36 (12H, br s), 3.71 (2H, br s), 7.44 (1H, dd, J=1.2 Hz, 8.6 Hz), 7.58 (1H, dd, J=2.2 Hz, 8.8 Hz), 7.70–7.79 (3H, m), 8.01 (1H, d, J=1.2 Hz)

IR (KBr): 2968, 1620, 1435, 1369, 1333, 895, 814 cm$^{-1}$.

(ii) Production of N,N-diisopropyl-6-[(1-trityl-1H-imidazol-4-yl)carbonyl)-2-naphthamide To anhydrous toluene (1000 ml) cooled to −70° C. was added butyl lithium (1.6 M; 98.3 ml), and then a solution of 6-bromo-N,N-diisopropyl-2-naphthamide (50.0 g) in dry THF (250 ml) was added dropwise. After stirring at −70° C. for 20 min, a solution of 1-trityl-1H-imidazol-4-ylcarbaldehyde (38.9 g) in dry THF (250 ml) was added dropwise to the reaction mixture. The mixture was stirred at −70° C. for 20 min and water was added at the same temperature to stop the reaction. The organic layer was separated and the aqueous layer was extracted with ethyl acetate. The organic layer was combined and the mixture was washed with saturated brine and dried over magnesium sulfate. The solvent was evaporated to give a yellow oily mixture containing 6-(hydroxy(1-trityl-1H-imidazol-4-yl)methyl]-N,N-diisopropyl-2-naphthamide.

This mixture and manganese dioxide (150 g) were suspended in dichloromethane (300 ml) and the suspension was stirred at room temperature for 90 min. The suspension was filtered through celite and the celite layer was washed with THF. The filtrate was concentrated under reduced pressure and the residue was recrystallized from ethanol to give the title compound (41.0 g) as a colorless powder.

$^1$H-NMR (CDCl$_3$) δ: 1.26–1.82 (12H, br d), 3.72 (2H, br s), 7.13–7.22 (6H, m), 7.34–7.42 (9H, m), 7.45 (1H, dd, J=1.4 Hz, 8.4 Hz), 7.58 (1H, d, J=1.4 Hz), 7.79–7.80 (2H, m), 7.90 (1H, d, J=8.8 Hz), 7.98 (1H, d, J=8.4 Hz), 8.29 (1H, dd, J=1.6 Hz, 8.8 Hz), 8.98 (1H, s)

IR (KBr): 2972, 1643, 1624, 1520, 1443, 1371, 1333, 1175, 756, 704 cm$^{-1}$.

Reference Example 14

Production of N,N-diisopropyl-6-[(1-trityl-1H-imidazol-4-yl)carbonyl]-2-naphthamide Dry toluene (20 ml) was cooled to −70° C. and n-butyl lithium (1.6 M; 2.35 ml) was added dropwise. A solution of 6-bromo-N,N-diisopropyl-2-naphthamide (1.20 g) in dry THF (8 ml) was added dropwise to the reaction mixture. After stirring the mixture at −70° C. for 20 min, a solution of N-methoxy-N-methyl-1-trityl-1H-imidazole-4-carboxyamide (1.09 g) in dry THF (6 ml) was added dropwise to the reaction mixture. The mixture was stirred at −70° C. for 20 min and water was added at the same temperature to stop the reaction. The mixture was extracted with ethyl acetate, and the organic layer was washed with saturated brine and dried over magnesium sulfate. The solvent was evaporated under reduced pressure and the residue was purified by column chromatography (hexane:ethyl acetate=2:1) to give the title compound (1.40 g) as a colorless powder. The physical and chemical data were identical with those obtained for the compound obtained of Reference Example 13.

Reference Example 15

Production of 6,7-dihydroimidazo[1,5-a]pyridin-8(5H)-one (i) Production of 4-(tetrahydro-2H-pyran-2-yloxy)-1-(1-trityl-1H-imidazol-4-yl)butan-1-one 4-(Tetrahydro-2H-pyran-2-yloxy)-1-(1-trityl-1H-imidazol-4-yl)-2-butyn-1-one (29.63 g) was dissolved in a mixture of ethyl acetate (200 ml) and tetrahydrofuran (800 ml). 10% Palladium carbon (2.6 g) was added and the mixture was stirred at room temperature for 3 h under a hydrogen atmosphere. 10% Palladium carbon was removed by filtration and the filtrate was concentrated under reduced pressure. The residue was purified by silica gel column chromatography (eluent; ethyl acetate) to give the title compound (28.53 g) as a brown solid.

$^1$H-NMR(CDCl$_3$) δ: 1.4–1.7 (6H, m), 1.9–2.1 (2H, m), 3.08 (2H, t, J=7.4 Hz), 3.4–3.55 (2H, m), 3.75–3.9 (2H, m), 4.55–4.6 (1H, m), 7.05–7.15 (6H, m), 7.3–7.4 (9H, m), 7.43 (1H, d, J=1.6 Hz), 7.57 (1H, d, J=1.6 Hz).

(ii) Production of 4-hydroxy-1-(1H-imidazol-4-yl)butan-1-one 4-(Tetrahydro-2H-pyran-2-yloxy)-1-(1-trityl-1H-imidazol-4-yl)butan-1-one (28.51 g) and 6 N hydrochloric acid (17.5 ml) were dissolved in tetrahydrofuran (200 ml) and the mixture was stirred at room temperature for 3 h. Sodium bicarbonate (8.82 g) was added to the reaction mixture, and after removal of the precipitate by filtration, the filtrate was concentrated under reduced pressure. The residue was purified by silica gel column chromatography (eluent; ethyl acetate:methanol=4:1) and recrystallized from methanol/ethyl acetate/diethyl ether to give the title compound (9.38 g) as a pale yellow powder.

$^1$H-NMR(CDCl$_3$+DMSO-d$_6$) δ: 1.93 (2H, m), 2.97 (2H, t, J=7.2 Hz), 3.62 (2H, t, J=6.4 Hz), 7.67 (1H, s), 7.72 (1H, s).

(iii) Production of 4-hydroxy-1-(1-trityl-1H-imidazol-4-yl)butan-1-one

4-Hydroxy-1-(1H-imidazol-4-yl)butan-1-one (9.23 g) was dissolved in N,N'-dimethylformamide (120 ml), and triethylamine (12.5 ml) and chlorotriphenylmethane (16.69 g) were added. The mixture was stirred at room temperature for 2 h. Brine was added and the mixture was extracted with ethyl acetate. The organic layer was dried over magnesium sulfate and concentrated under reduced pressure. The residue was purified by silica gel column chromatography (eluent; ethyl acetate:hexane=9:1) to give the title compound (25.22 g) as an orange oil.

$^1$H-NMR(CDCl$_3$) δ: 1.95–2.05 (2H, m), 3.10 (2H, t, J=6.4 Hz), 3.2–3.3 (1H, m), 3.6–3.75 (2H, m), 7.05–7.15 (6H, m), 7.3–7.4 (9H, m), 7.45 (1H, d, J=1.0 Hz), 7.58 (1H, d, J=1.0 Hz).

(iv) Production of 6,7-dihydroimidazo[1,5-a]pyridin-8(5H)-one

4-Hydroxy-1-(1-trityl-1H-imidazol-4-yl)butan-1-one (25.22 g) was dissolved in tetrahydrofuran (120 ml). Triethylamine (0.021 ml) and methanesulfonyl chloride (0.012 ml) were added and the mixture was stirred at room temperature for 1 h. Water (100 ml) was added under ice-cooling and the mixture was extracted with ethyl acetate. The organic layer was dried over magnesium sulfate and concentrated under reduced pressure. Acetonitrile (100 ml) was added and the mixture was refluxed under heating for 2 h. The reaction mixture was concentrated to dryness and the residue was purified by silica gel column chromatography (eluent; ethyl acetate:methanol=20:1→5:1) and washed with diethyl ether to give the title compound (2.10 g) as a pale-brown powder.

$^1$H-NMR(CDCl$_3$) δ: 2.25–2.35 (2H, m), 2.66 (2H, t, J=6.2 Hz), 4.21 (2H, t, J=5.8 Hz), 7.63 (1H, s), 7.83 (1H, s).

IR(KBr): 1485, 1387, 1265, 1202, 1028, 856 cm$^{-1}$.

Example 1

Production of 7-(5-methoxybenzo[b]thiophen-2-yl)-6,7-dihydro-5H-pyrrolo[1,2-c]imidazol-7-ol

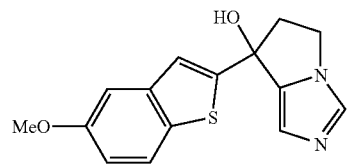

A solution of 5-methoxybenzo[b]thiophene (0.33 g) in THF (8 ml) was cooled to −78° C., and an n-butyl lithium hexane solution (1.6 M; 1.4 ml) was added dropwise to this solution. The mixture was stirred for 1 h at the same temperature, and a solution of 5,6-dihydro-7H-pyrrolo[1,2-c]imidazol-7-one (0.18 g) in THF (3 ml) was added to this solution. The reaction mixture was stirred for 1 h at the same temperature, and saturated brine was added. The mixture was warmed to room temperature and the organic layer was separated. The organic layer was diluted with ethyl acetate, washed with saturated brine and dried over anhydrous magnesium sulfate. The solvent was evaporated. The residue was suspended in ethyl acetate and filtrated to give the title compound (0.24 g) as pale brown crystals. The crystals were recrystallized from THF to give the title compound (0.13 g) as colorless crystals.

$^1$H-NMR (CDCl$_3$+CD$_3$OD) δ: 3.02 (2H, dd, J=7.8 Hz, 6.0 Hz), 3.86 (3H, s), 4.09–4.37 (2H, m), 6.93 (1H, s), 6.97 (1H, dd, J=8.8 Hz, 2.6 Hz), 7.16 (1H, d, J=2.6 Hz), 7.17 (1H, s), 7.49 (1H, s), 7.67 (1H, d, J=8.8 Hz).

IR (KBr): 3115, 1462, 1223, 1028, 856, 845, 799, 669 cm$^{-1}$.

Example 2

Production of 7-(5-fluorobenzo[b]thiophen-2-yl)-6,7-dihydro-5H-pyrrolo[1,2-c]imidazol-7-ol

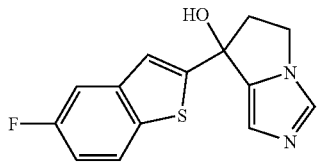

The reaction and purification in the same manner as in Example 1 using 5-fluorobenzo[b]thiophene (0.30 g) and 5,6-dihydro-7H-pyrrolo[1,2-c]imidazol-7-one (0.18 g) afforded the title compound (0.14 g) as colorless crystals.

$^1$H-NMR (CDCl$_3$+CD$_3$OD) δ: 3.03 (2H, dd, J=7.6 Hz, 5.4 Hz), 4.10–4.40 (2H, m), 6.93 (1H, s), 7.08 (1H, dt, J=2.6 Hz, 8.8 Hz), 7.20 (1H, s), 7.37 (1H, dd, J=9.6 Hz, 2.6 Hz), 7.52 (1H, s), 7.74 (1H, dd, J=8.8 Hz, 4.8 Hz).

IR (KBr): 3121, 1445, 1215, 1088, 947, 866, 810, 802 cm$^{-1}$.

Example 3

Production of 7-(4'-fluoro[1,1'-biphenyl]-3-yl)-6,7-dihydro-5H-pyrrolo[1,2-c]imidazol-7-ol

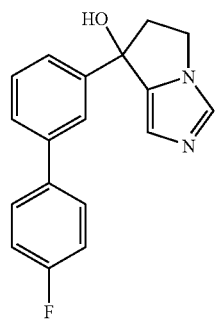

A solution (1.6 M; 1.98 ml) of n-butyl lithium in hexane was gently added dropwise to a solution of 3-bromo-4'-fluoro-1,1'-biphenyl (753 mg) in THF (10 ml) at −78° C., and the mixture was stirred at −78° C. for 30 min. A solution of 5,6-dihydro-7Hpyrrolo[1,2-c]imidazol-7-one (244 mg) in THF (10 ml) solution was gently added dropwise and the mixture was stirred at −78° C. for 1 h. A saturated aqueous ammonium chloride solution was added to the reaction mixture and the mixture was extracted with ethyl acetate, washed with saturated brine, and dried over anhydrous magnesium sulfate. The solvent was evaporated under reduced pressure and the residue was purified by silica gel column chromatography (eluent, ethyl acetate→ethyl acetate:methanol=5:1) and recrystallized from acetone-hexane to give the title compound (265 mg) as colorless needle crystals.

$^1$H-NMR (CDCl$_3$+CD$_3$OD) δ: 2.79–2.93 (2H, m), 4.14 (1H, ddd, J=3.6 Hz, 7.2 Hz, 10.6 Hz), 4.25–4.38 (1H, m), 6.79 (1H, s), 7.16 (2H, dd, J=8.8 Hz, 8.8 Hz), 7.39–7.58 (6H, m), 7.55 (1H, s).

IR (KBr): 3058, 1510, 1217, 837, 820, 808, 795 cm$^{-1}$.

Example 4

Production of 7-(4'-fluoro[1,1'-biphenyl]-4-yl)-6,7-dihydro-5H-pyrrolo[1,2-c]imidazol-7-ol

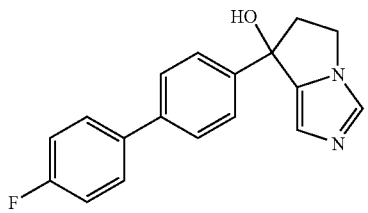

(i) Production of 7-(4-bromophenyl)-6,7-dihydro-5H-pyrrolo[1,2-c]imidazol-7-ol

The reactions in the same manner as in Example 3 using p-dibromobenzene (3.94 g), a hexane solution (1.6 M; 8.70 ml) of n-butyl lithium, and 5,6-dihydro-7H-pyrrolo[1,2-c]imidazol-7-one (850 mg) afforded the title compound (1.03 g) as colorless plate crystals.

$^1$H-NMR (CDCl$_3$) δ: 2.67–2.94 (2H, m), 4.08 (1H, ddd, J=2.6 Hz, 8.0 Hz, 11.0 Hz), 4.19–4.32 (1H, m), 5.47 (1H, br s), 6.52 (1H, s), 7.31 (1H, s), 7.39–7.51 (4H, m).

IR (KBr): 1493, 1395, 1084, 1011, 914, 829, 806, 733, 654 cm$^{-1}$.

(ii) Production of 7-(4'-fluoro[1,1'-biphenyl]-4-yl)-6,7-dihydro-5H-pyrrolo[1,2-c]imidazol-7-ol The reactions in the same manner as in Reference Example 10 using 7-(4-bromophenyl)-6,7-dihydro-5H-pyrrolo[1,2-c]imidazol-7-ol (982 mg), 4-fluorophenylboronic acid (738 mg), 2M aqueous sodium carbonate solution (3.52 ml) and tetrakis(triphenylphosphine)palladium(0) (122 mg) afforded the title compound (393 mg) as colorless powder crystals.

$^1$H-NMR (CDCl$_3$+CD$_3$OD) δ: 2.79–2.99 (2H, m), 4.16 (1H, ddd, J=4.0 Hz, 7.4 Hz, 11.0 Hz), 4.26–4.40 (1H, m), 6.82 (1H, s), 7.14 (2H, dd, J=8.8 Hz, 8.8 Hz), 7.53–7.64 (7H, m).

IR (KBr): 1321, 1495, 1086, 826, 802 cm$^{-1}$.

Example 5

Production of 6-(7-hydroxy-6,7-dihydro-5H-pyrrolo[1,2-c]imidazol-7-yl)-N-methyl-2-naphthamide

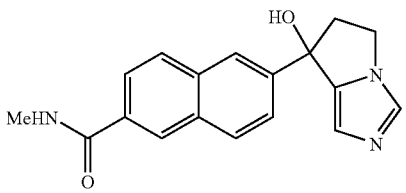

Dry THF (150 ml) was cooled to −65° C. in a dry ice-acetone bath under an argon atmosphere and n-butyl lithium hexane solution (1.6M: 45.2 ml) was added. A solution of 6-bromo-N-methyl-2-naphthamide (8.68 g) in dry THF (700 ml) cooled to 10° C. was added to this solution at not more than −55° C., and the mixture was stirred for 1 h. A dry THF solution (60 ml) of 5,6-dihydro-7H-pyrrolo[1,2-c]imidazol-7-one (3.65 g) was added dropwise. The mixture was stirred at the same temperature for 1.5 h and saturated aqueous ammonium chloride solution (120 ml) was added to stop the reaction. The solvent was evaporated under reduced pressure and an ethanol-soluble material was extracted from the resulting residue and the solvent was evaporated again. The residue was purified by flash silica gel column chromatography (eluent, chloroform/methanol containing ammonia (7%), 19/1→9/1). The eluate was recrystallized from methanol to give the title compound (3.36 g) as colorless crystals.

$^1$H-NMR(CDCl$_3$+CD$_3$OD) δ: 2.89–3.02 (2H, m), 3.04 (3H, s), 4.12–4.25 (1H, m), 4.27–4.43 (1H, m), 6.79 (1H, s), 7.20 (1H, q, J=4.6 Hz), 7.54 (1H, s), 7.63 (1H, dd, J=1.8 Hz, 8.6 Hz), 7.83 (2H, s), 7.89 (1H, d, J=8.6 Hz), 8.03 (1H, s), 8.28 (1H, s).

IR(KBr): 3500–3000, 1644, 1605, 1559, 1497, 1464, 1318, 1082 cm$^{-1}$.

Example 6

Production of N-cyclopropyl-6-(7-hydroxy-6,7-dihydro-5Hpyrrolo[1,2-c]imidazol-7-yl)-2-naphtha

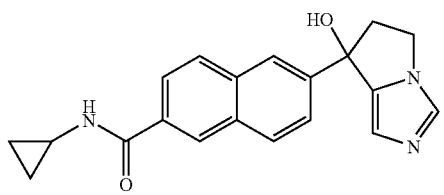

Under an argon atmosphere, 6-bromo-N-cyclopropyl-2-naphthamide (320 mg) was dissolved in dry tetrahydrofuran (11 ml), and the mixture was cooled to −70° C. in a dry ice-acetone bath. An n-butyl lithium hexane solution (1.6M: 1.52 ml) was added and the mixture was stirred for 1.5 h. A dry tetrahydrofuran solution (3 ml) of 5,6-dihydro-7H-pyrrolo[1,2-c]imidazol-7-one (123 mg) was added dropwise. The mixture was stirred at the same temperature for 1.5 h and saturated aqueous ammonium chloride solution (4 ml) was added to stop the reaction. The solvent was evaporated under reduced pressure and an ethanol-soluble material was extracted from the resulting residue and the solvent was evaporated again. The resulting residue was purified by flash silica gel column chromatography (eluent; chloroform/methanol containing ammonia (7%); 19/1). The eluate was recrystallized from methanol to give the title compound (100 mg) as a colorless crystalline powder.

$^1$H-NMR(DMSO-d$_6$) δ: 0.58–0.79 (4H, m), 2.75–3.00 (3H, m), 4.12–4.32 (2H, m), 6.17 (1H, s), 6.66 (1H, s), 7.63 (1H, dd, J=1.4 Hz, 8.8 Hz), 7.64 (1H, s), 7.90 (1H, dd, J=1.4 Hz, 8.6 Hz), 7.98 (2H, d, J=8.6 Hz), 8.05 (1H, s), 8.39 (1H, s), 8.61 (1H, d, J=4.4 Hz).

IR(KBr): 3258, 1644, 1630, 1603, 1541, 1495, 1316, 1080 cm$^{-1}$.

Example 7

Production of N-ethyl-6-(7-hydroxy-6,7-dihydro-5H-pyrrolo[1,2-c]imidazol-7-yl)-2-naphthamide

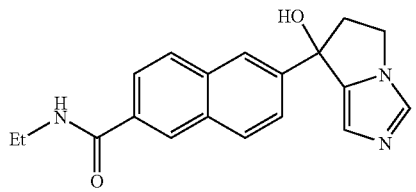

The reactions in the same manner as in Example 6 using 6-bromo-N-ethyl-2-naphthamide (459 mg), an n-butyl lithium hexane solution (1.6M: 2.28 ml) and 5,6-dihydro-7H-pyrrolo[1,2-c]imidazol-7-one (183 mg) afforded the title compound (142 mg) as a colorless crystalline powder.

$^1$H-NMR(CDCl$_3$+CD$_3$OD) δ: 1.29 (3H, t, J=7.2 Hz), 2.85–3.06 (2H, m), 3.46–3.60 (2H, m), 4.10–4.24 (1H, m), 4.27–4.41 (1H, m), 6.88 (1H, s), 6.89 (1H, t, J=5.2 Hz), 7.50 (1H, s), 7.62 (1H, dd, J=1.6 Hz, 8.6 Hz), 7.81 (2H, s), 7.87 (1H, d, J=8.6 Hz), 8.02 (1H, s), 8.26 (1H, s).

IR(KBr): 3283, 1642, 1605, 1557, 1495, 1447, 1316, 1080 cm$^{-1}$.

Example 8

Production of N-cyclobutyl-6-(7-hydroxy-6,7-dihydro-5H-pyrrolo[1,2-c]imidazol-7-yl)-2-naphthamide

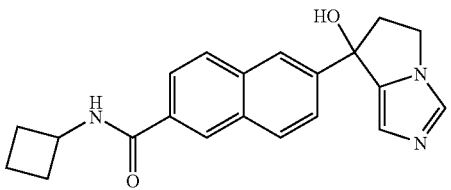

The reactions in the same manner as in Example 6 using 6-bromo-N-cyclobutyl-2-naphthamide (502 mg), a 1.6 M n-butyl lithium/hexane solution (2.28 ml) and 5,6-dihydro-7H-pyrrolo[1,2-c]imidazol-7-one (183 mg) afforded the title compound (203 mg) as a colorless crystalline powder.

$^1$H-NMR(CDCl$_3$+CD$_3$OD) δ: 1.73–1.90 (2H, m), 1.95–2.17 (2H, m), 2.38–2.55 (2H, m), 2.86–3.04 (2H, m), 4.10–4.24 (1H, m), 4.27–4.43 (1H, m), 4.53–4.73 (1H, m), 6.78 (1H, s), 6.95 (1H, d, J=3.8 Hz), 7.52 (1H, s), 7.64 (1H, dd, J=1.6 Hz, 8.8 Hz), 7.83 (2H, s), 7.89 (1H, d, J=8.8 Hz), 8.03 (1H, s), 8.26 (1H, s).

IR(KBr): 3320, 1626, 1601, 1549, 1495, 1314, 1092 cm$^{-1}$.

Example 9

Production of 6-(7-hydroxy-6,7-dihydro-5H-pyrrolo[1,2-c]imidazol-7-yl)-N-isopropyl-2-naphthamide

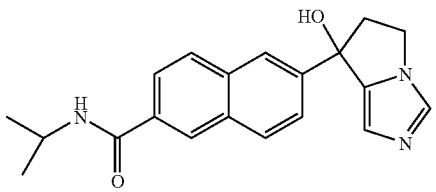

The reactions in the same manner as in Example 6 using 6-bromo-N-isopropyl-2-naphthamide (482 mg), a 1.6 M n-butyl lithium/hexane solution (2.28 ml) and 5,6-dihydro-7H-pyrrolo[1,2-c]imidazol-7-one (183 mg) afforded the title compound (187 mg) as a colorless crystalline powder.

$^1$H-NMR(CDCl$_3$+CD$_3$OD) δ: 1.31 (6H, d, J=6.4 Hz), 2.87–3.06 (2H, m), 4.12–4.26 (1H, m), 4.27–4.44 (1H, m), 6.56 (1H, d, J=7.8 Hz), 6.78 (1H, s), 7.52 (1H, s), 7.64 (1H, dd, J=1.8 Hz, 8.8 Hz), 7.82 (2H, s), 7.89 (1H, d, J=8.8 Hz), 8.03 (1H, s), 8.25 (1H, s).

IR(KBr): 3277, 1640, 1628, 1603, 1557, 1493, 1350, 1080 cm$^{-1}$.

Example 10

Production of 6-(7-hydroxy-6,7-dihydro-5H-pyrrolo[1,2-c]imidazol-7-yl)-N-methyl-2-naphthamide

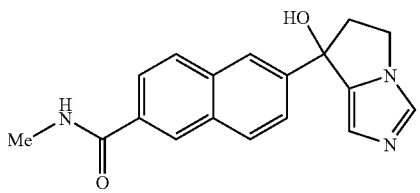

Under an argon atmosphere, 2-bromobenzotrifluoride (33.05 g) was dissolved in dry THF (600 ml), and the mixture was cooled to −65° C. in a dry ice-acetone bath. An n-butyl lithium hexane solution (1.6M: 93.7 ml) was added with stirring and the mixture was stirred at the same temperature for 30 min. After stirring the mixture, a dry THF (2.88L) solution of 6-bromo-N-methyl-2-naphthamide (38.03 g) cooled to 10° C. was added at not more than −55° C. The mixture was stirred for 20 min. An n-butyl lithium hexane solution (1.6M: 94.5 ml) was added at not more than −65° C. The mixture was stirred for 30 min and 5,6-dihydro-7H-pyrrolo[1,2-c]imidazol-7-one (14.66 g) in a dry THF solution (240 ml) was added dropwise. The mixture was stirred at the same temperature for 1.5 h and saturated aqueous ammonium chloride solution (520 ml) was added to stop the reaction. The solvent was evaporated under reduced pressure and an ethanol-soluble material was extracted from the resulting residue and the solvent was evaporated again. The resulting residue was purified by flash silica gel column chromatography (eluent; chloroform/methanol containing ammonia (7%); 19/1→9/1). The eluate was recrystallized from methanol to give the title compound (16.44 g) as colorless crystals. The physical and chemical data were identical with those of the compound obtained in Example 5.

Example 11

Production of (+)-6-(7-hydroxy-6,7-dihydro-5H-pyrrolo[1,2-c]imidazol-7-yl)-N-methyl-2-naphthamide (1)

6-(7-Hydroxy-6,7-dihydro-5H-pyrrolo[1,2-c]imidazol-7-yl)-N-methyl-2-naphthamide was subjected to chromatography (eluent:hexane-ethanol=1:1) using an optical isomer separation column (CHIRALPAK AD: manufactured by Daicel Chemical Industries, Ltd.). As the second elution, (+)-6-(7-hydroxy-6,7-dihydro-5H-pyrrolo[1,2-c]imidazol-7-yl)-N-methyl-2-naphthamide was obtained.

enantiomer excess >99% ee
$[α]_D^{20}$ +83.1° (C=0.997, methanol)

Example 12

Production of (+)-6-(7-hydroxy-6,7-dihydro-5H-pyrrolo[1,2-c]imidazol-7-yl)-N-methyl-2-naphthamide (2)

A racemate (2.0 g) of 6-(7-hydroxy-6,7-dihydro-5H-pyrrolo[1,2-c]imidazol-7-yl)-N-methyl-2-naphthamide and (2S,3S)-(−)-tartranilic acid (2.9 g) were added to ethanol (60 ml) and dissolved by heating (50° C.). The mixture was stirred at room temperature for 15 h and a precipitated salt was collected by filtration and washed by sprinkling ethanol (3.0 ml).

The salt was dried under reduced pressure at 50° C. for 3 h to give 2.4 g of colorless crystals (yield 97%). At this point, 6-(7-hydroxy-6,7-dihydro-5H-pyrrolo[1,2-c]imidazol-7-yl)-N-methyl-2-naphthamide and (2S,3S)-(−)-tartranilic acid formed a salt having a molar ratio of 1:2. As a result of HPLC analysis, the diastereomer excess was 90% de.

Ethanol (25 ml) was added to the crystals (1.0 g) obtained above to dissolve by heating (50° C.). The mixture was stirred at room temperature for 15 h and a precipitated salt was collected by filtration and washed by sprinkling ethanol (2.0 ml). The yield was 807 mg (yield 81%). As a result of HPLC analysis, the diastereomer excess was 99% de.

Melting point; 129–130° C.
specific rotation; $[α]_D^{26}$=−39.4° (c=0.5 in methanol)

1N Sodium hydroxide (1.0 ml) was added to the crystals (100 mg). The mixture was stirred at room temperature for 1 h, filtrated and washed by sprinkling water (0.3 ml). The reaction mixture was dried under reduced pressure at 60° C. for 3 h to give 36.8 mg of crystals (yield 91%, overall yield 71%). As a result of HPLC analysis, the enantiomer excess was 99% ee.

$^1$H-NMR(DMSO-d$_6$) δ: 2.84–2.95 (5H, m), 4.18–4.27 (2H, m), 6.15 (1H, s), 6.66 (1H, s), 7.62–7.64 (2H, m), 7.91–8.06 (4H, m), 8.41 (1H, s), 8.59 (1H, br)

Example 13

Production of diastereomeric salt of 6-(7-hydroxy-6,7-dihydro-5H-pyrrolo[1,2-c]imidazol-7-yl)-N-methyl-2-naphthamide with (2S,3S)-(−)-tartranilic Acid A racemate (100 mg) of 6-(7-hydroxy-6,7-dihydro-5H-pyrrolo[1,2-c]imidazol-7-yl)-N-methyl-2-naphthamide and (2S,3S)-(−)-tartranilic acid (146.4 mg) were added to ethanol (3.5 ml) and dissolved by heating. The mixture was stirred at room temperature overnight and a precipitated product was isolated by filtration to give 114.1 mg of crystals (yield 93%). As a result of HPLC analysis, the diastereomer excess was 71% de. Of the crystals, 113 mg was recrystallized from ethanol (3.0 ml) to give 79.0 mg of crystals (yield 70%). As a result of HPLC analysis, the diastereomer excess was 96% de. Of the crystals, 78.5 mg was recrystallized from 1-propanol (3.0 ml) to give 52.8 mg of crystals (yield 67%, overall yield 44%). At this point, (+)-6-(7-hydroxy-6,7-dihydro-5H-pyrrolo[1,2-c]imidazol-7-yl)-N-methyl-2-naphthamide and (2S,3S)-(−)-tartranilic acid formed a salt having a molar ratio of 1:2. As a result of HPLC analysis, the diastereomer excess was 98% de.

Example 14

Production of Diastereomeric Salt of 6-(7-hydroxy-6,7-dihydro-5H-pyrrolo[1,2-c]imidazol-7-yl)-N-methyl-2-naphthamide with (2S,3S)-(−)-tartranilic Acid A racemate (100 mg) of 6-(7-hydroxy-6,7-dihydro-5H-pyrrolo[1,2-c]imidazol-7-yl)-N-methyl-2-naphthamide and (2S,3S)-(−)-tartranilic acid (146.4 mg) were dissolved in 2-propanol (6.0 ml) by heating. The mixture was stood at room temperature overnight and a precipitated product was isolated by filtration to give 165.7 mg of crystals (yield 134%). As a result of HPLC analysis, the diastereomer excess was 26% de. Of the crystals, 165 mg was recrystallized from ethanol (4.0 ml) to give 87.8 mg of crystals (yield 53%). As a result of HPLC analysis, the diastereomer excess was 89% de. Of the crystals, 87 mg was recrystallized from 1-propanol (3.5 ml) to give 58.0 mg of crystals (yield 67%, overall yield 47%). As a result of HPLC analysis, the diastereomer excess was 97% de.

Example 15

Production of Diastereomeric Salt of 6-(7-hydroxy-6,7-dihydro-5H-pyrrolo[1,2-c]imidazol-7-yl)-N-methyl-2-naphthamide with (2S,3S)-(−)-tartranilic Acid A racemate (100 mg) of 6-(7-hydroxy-6,7-dihydro-5H-pyrrolo[1,2-c]imidazol-7-yl)-N-methyl-2-naphthamide and (2S,3S)-(−)-tartranilic acid (73.2 mg) were dissolved in 1-propanol (4.0 ml) by heating. A seed crystal of 98% de was added and the mixture was stirred at room temperature overnight. The precipitated product was isolated by filtration to give 100.3 mg of crystals (yield 81%). As a result of HPLC analysis, the diastereomer excess was 89% de. Of the crystals, 86.8 mg was refluxed in ethanol (1.0 ml) and 2-propanol (1.0 ml) for 20 min and stood at room temperature as it was. Three(3) days later, the precipitated product was filtrated to give 72.4 mg of crystals (yield 83%, overall yield 67%). At this point, 6-(7-hydroxy-6,7-dihydro-5H-pyrrolo[1,2-c]imidazol-7-yl)-N-methyl-2-naphthamide and (2S,3S)-(−)-tartranilic acid formed a salt having a molar ratio 1:2. As a result of HPLC analysis, the diastereomer excess was 99% de.

$^1$H-NMR(DMSO-$d_6$) δ: 2.84–2.94 (5H, m), 4.17–4.28 (2H, m), 4.38–4.40 (4H, m), 6.20 (1H, br), 6.70 (1H, s), 7.04–7.08 (2H, t, J=7.3 Hz), 7.28–7.32 (4H, dd, J=7.3 Hz, 7.6 Hz), 7.62–7.70 (6H, m), 7.91–8.06 (4H, m), 8.40 (1H, s), 8.50 (1H, s), 9.55 (2H, s)

Example 16

Production of Diastereomeric Salt of 6-(7-hydroxy-6,7-dihydro-5H-pyrrolo[1,2-c]imidazol-7-yl)-N-methyl-2-naphthamide with (2S,3S)-(−)-tartranilic Acid A racemate (50 mg) of 6-(7-hydroxy-6,7-dihydro-5H-pyrrolo[1,2-c]imidazol-7-yl)-N-methyl-2-naphthamide and (2S,3S)-(−)-tartranilic acid (36.6 mg) was dissolved in 2-propanol (0.5 ml) and tetrahydrofuran (0.5 ml) under heating. The mixture was stirred at room temperature overnight. The precipitated product was isolated by filtration to give 43.6 mg of crystals (yield 71%). At this point, 6-(7-hydroxy-6,7-dihydro-5H-pyrrolo[1,2-c]imidazol-7-yl)-N-methyl-2-naphthamide and (2S,3S)-(−)-tartranilic acid formed a salt having a molar ratio 1:2. As a result of HPLC analysis, the diastereomer excess was 48% de.

Example 17

Production of 6-(7-hydroxy-6,7-dihydro-5H-pyrrolo[1,2-c]imidazol-7-yl)-2-naphthamide

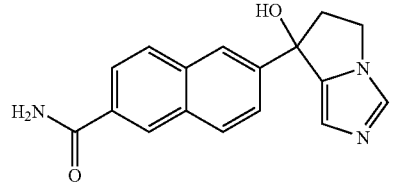

(i) Production of 6-(7-hydroxy-6,7-dihydro-5H-pyrrolo[1,2-c]imidazol-7-yl)-2-naphthoic Acid 6-Bromo-2-naphthoic acid (1.51 g) was dissolved in dry THF (50 ml) and the mixture was cooled in a liquid nitrogen/diethyl ether bath to −100° C. With stirring the mixture, an n-butyl lithium hexane solution (1.6M; 7.88 ml) was added dropwise at not more than −95° C. over 5 min. The mixture was stirred at −100° C. for 30 min and at −80° C. for 10 min. Thereafter, the mixture was cooled again to −100° C. and a solution of 5,6-dihydro-7H-pyrrolo[1,2-c]imidazol-7-one (0.61 g) in dry THF (11 ml) was added dropwise at not more than −90° C. over 5 min. The mixture was stirred at same temperature for 30 min and warmed to −70° C. over 30 min. A saturated aqueous ammonium chloride solution (25 ml) was added to stop the reaction. After stirring the mixture for 10 min, ethyl acetate (50 ml) was added for partitioning. The organic layer was removed and the aqueous layer was concentrated to dryness. The resulting residue was purified by flash column chromatography and the objective fraction was dissolved in methanol. This solution was concentrated, ether was added to the precipitated powder for filtration and dried to give the title compound (180 mg) as a colorless powder. The mother liquid was concentrated to give a residue (449 mg) containing the title compound.

$^1$H-NMR(CD$_3$OD) δ: 2.87–3.13 (2H, m), 4.28–4.50 (2H, m), 6.94 (1H, s), 7.65 (1H, dd, J=1.6 Hz, 8.6 Hz), 7.90 (1H, d, J=8.4 Hz), 7.99 (1H, d, J=8.6 Hz), 8.01 (1H, s), 8.06 (1H, dd, J=1.4 Hz, 8.4 Hz), 8.09 (1H, s), 8.57 (1H, s).

IR(KBr): 3500–3000, 1698, 1609, 1551, 1480, 1397, 1325, 1086 cm$^{-1}$.

FAB-Mass: 295(MH$^+$)

ii) Production of 6-(7-hydroxy-6,7-dihydro-5H-pyrrolo[1,2-c]imidazol-7-yl)-2-naphthamide 6-(7-Hydroxy-6,7-dihydro-5H-pyrrolo[1,2-c]imidazol-7-yl)-2-naphthoic acid (449 mg), 1-ethyl-3-(3-dimethylaminopropyl)-carbodiimide hydrochloride (321 mg) and 1-hydroxy-1H-benzotriazole monohydrate (301 mg) were dissolved in DMF (7.6 ml), and diisopropylethylamine (216 mg) was added with stirring under ice-cooling. The reaction mixture was warmed to room temperature and stirred for 18 h. Silica gel (3 g) was added to the reaction mixture and the mixture was concentrated to dryness under reduced pressure. The resulting residue was purified by silica gel column chromatography (eluent: chloroform/methanol containing aqueous ammonia (7%): 19/1) and the eluate was concentrated to dryness. The residue was recrystallized from ethanol to give the title compound (53 mg).

$^1$H-NMR(CDCl$_3$+CD$_3$OD) δ: 2.94–3.00 (2H, m), 4.15–4.40 (2H, m), 6.82 (1H, s), 7.58 (1H, s), 7.66 (1H, dd, J=1.8 Hz, 8.6 Hz), 7.90 (2H, s), 7.95 (1H, d, J=8.6 Hz), 8.07 (1H, s), 8.40 (1H, s).

IR(KBr): 3345, 1663, 1618, 1599, 1493, 1414, 1080 cm$^{-1}$.

elemental analysis:
calculated; C$_{17}$H$_{15}$N$_3$O$_2$.H$_2$O; C65.58; H5.50; N13.50.
found; C65.63; H5.50; N13.73.

Example 18

Production of 6-(7-hydroxy-6,7-dihydro-5H-pyrrolo[1,2-c]imidazol-7-yl)-N-methyl-2-naphthamide

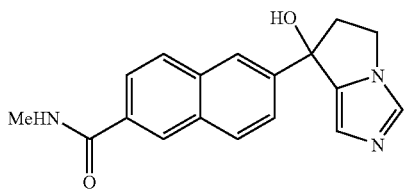

(i) Production of ethyl 3-{6-[(diisopropylamino)carbonyl]-2-naphthtyl}-3-hydroxy-3-(1-trityl-1 H-imidazol-4-yl)propionate Dry THF (600 ml) containing diisopropylamine (21.3 ml) was cooled to –70° C. and n-butyl lithium (1.6 M; 95.0 ml) was added dropwise. The mixture was stirred for 10 min and ethyl acetate (14.9 ml) was added dropwise. The mixture was stirred at the same temperature for 30 min. A solution of N,N-diisopropyl-6-[(1-trityl-1H-imidazol-4-yl)carbonyl]-2-naphthamide (60.0 g) in dry THF (150 ml) was added dropwise at –70° C. The mixture was stirred at the same temperature for 30 min and the reaction mixture was gradually warmed to –30° C. Water was added to stop the reaction. The organic layer was separated and the aqueous layer was extracted with a THF-toluene (1:1) mixture. The organic layers were combined, washed with saturated brine and dried over magnesium sulfate. The solvent was evaporated to give the title compound quantitatively as a pale yellow oil.

$^1$H-NMR (CDCl$_3$) δ: 1.14 (3H, t, J=7.0 Hz), 1.34 (12H, br s), 3.17 (1H, d, J=16.2 Hz), 3.50 (1H, d, J=16.2 Hz), 3.72 (2H, br s), 3.08 (2H, q, J=7.0 Hz), 5.15 (1H, s), 6.84 (1H, s), 7.07–7.14 (6H, m), 7.26–7.34 (9H, m), 7.378 (1H, d, J=1.4 Hz), 7.380 (1H, dd, J=1.7 Hz, 8.3 Hz), 7.68 (1H, dd, J=1.8 Hz, 8.8 Hz), 7.74–7.84 (3H, m), 8.03 (1H, d, J=1.0 Hz).

IR (KBr): 3454, 2968, 1705, 1636, 1371, 1337, 1213, 746, 704 cm$^{-1}$.

(ii) Production of 6-[1,3-dihydroxy-1-(1-trityl-1H-imidazol-4-yl)propyl]-N,N-diisopropyl-2-naphthamide Ethyl 3-{6-[(diisopropylamino)carbonyl]-3-naphthtyl}-3-hydroxy-2-(1-trityl-1 H-imidazo-4-yl)propionate obtained in the previous step was dissolved in dry toluene (600 ml) and cooled to –15° C. Dihydro-bis(2-methoxyethoxy)aluminum sodium (Red-Al™: 65% toluene solution; 110 ml) was added dropwise to the reaction mixture while maintaining the temperature of the reaction mixture at not more than 0° C. The mixture was stirred at –10° C. –0° C. for 2.5 h. The reaction mixture was cooled to –10° C. and water (12.5 ml) was gently added dropwise. THF (300 ml) was added, and 15% aqueous sodium hydroxide solution (12 ml) and water (36 ml) were added and the mixture was stirred 10 min. Celite was added and the mixture was stirred for 10 min. The suspension was filtrated and the celite layer was washed with THF. The filtrate was washed successively with 10% aqueous citric acid solution, water, saturated sodium bicarbonate solution and saturated brine and dried over magnesium sulfate. The solvent was evaporated and the resulting residue was recrystallized from hexane-ethyl acetate to give the title compound (63.7 g) as a colorless powder.

$^1$H-NMR (CDCl$_3$) δ: 1.34 (12H, br s), 2.27–2.40 (1H, m), 2.48–2.61 (1H, m), 3.70 (2H, t, J=5.0 Hz), 3.83 (3H, br s), 4.54 (1H, s), 6.78 (1H, d, J=1.6 Hz), 7.08–7.17 (6H, m), 7.28–7.40 (11H, m), 7.51 (1H, dd, J=1.8 Hz, 8.4 Hz), 7.71–7.81 (3H, m), 7.97 (1H, s).

IR (KBr): 3497, 3200, 2964, 1634, 1445, 1335, 748, 702 cm$^{-1}$.

(iii) Production of 6-(7-hydroxy-6,7-dihydro-5H-pyrrolo[1,2-c]imidazol-7-yl)-N,N-diisopropyl-2-naphthamide 6-[1,3-Dihydroxy-1-(1-trityl-1H-imidazol-4-yl)propyl]-N,N-diisopropyl-2-naphthamide (63.0 g) and ethyl diisopropylamine (34.5 ml) were dissolved in dry THF (400 ml) and cooled to 0° C. Methanesulfonyl chloride (9.21 ml) was added dropwise while maintaining the temperature of the reaction mixture at not more than 10° C. The mixture was stirred at 0° C. for 30 min water was added to stop the reaction. The reaction mixture was extracted with ethyl acetate and the organic layer was washed with saturated brine and dried over magnesium sulfate. The solvent was evaporated under reduced pressure to give a reddish amorphous mixture containing 3-{6-[(diisopropylamino)carbonyl]-2-naphthtyl}-3-hydroxy-3-(1-trityl-1H-imidazol-4-yl) propyl methane sulfonate.

The above-mentioned mixture was dissolved in acetonitrile (300 ml) and the mixture was stirred at 70° C. for 20 min. Methanol (100 ml) and ethyldiisopropylamine (34.5 ml) were added to the reaction mixture and the mixture was stirred at 70° C. for 6 h. The solvent was evaporated to make the amount to about a half and diluted with water, and extracted with ethyl acetate. The organic layer was washed with saturated brine and the solvent was evaporated. The resulting residue was dissolved in ethyl acetate (60 ml) by heating and left standing. The resulting crystals were filtrated and washed with ethyl acetate to give the title compound (32.5 g) as a colorless powder.

$^1$H-NMR (CDCl$_3$) δ: 1.18–1.50 (12H, br d), 2.78–2.97 (2H, m), 3.69–3.77 (2H, br d), 4.01–4.09 (1H, m), 4.18–4.28 (1H, m), 6.58 (1H, s), 7.26 (1H, s), 7.36 (1H, dd, J=1.2 Hz, 5.6 Hz), 7.59 (1H, dd, J=1.2 Hz, 5.8 Hz), 7.72–7.78 (3H, m), 7.99 (1H, s).

IR (KBr): 3275, 2964, 1611, 1487, 1450, 1371, 1342, 800 cm$^{-1}$.

(iv) Production of 6-(7-hydroxy-6,7-dihydro-5H-pyrrolo[1,2-c]imidazol-7-yl)-N-methyl-2-naphthamide Methylamine (2M in THF, 200 ml) was dissolved in dry THF (300 ml) and the mixture was cooled to −70° C. n-Butyl lithium (1.6 M; 250 ml) was added dropwise and the mixture was stirred at the same temperature for 20 min. The above-mentioned solution was added to a suspension (600 ml) of 6-(7-hydroxy-6,7-dihydro-5H-pyrrolo[1,2-c]imidazol-7-yl)-N,N-diisopropyl-2-naphthamide (37.7 g) in dry THF with a Teflon needle while stirring the mixture under ice-cooling, and the mixture was stirred at room temperature for 16 h. The saturated brine and water were added to the reaction mixture, and the mixture was diluted with ethyl acetate. The mixture was stirred for 10 min and the precipitated crystals were filtrated. The organic layer of the filtrate was separated and the aqueous layer was extracted with THF/ethyl acetate (1:1) mixture. The organic layers were combined and dried over sodium sulfate. The solvent was evaporated under reduced pressure and the residue was dissolved in THF-ethyl acetate (1:1). The precipitated crystals were collected by filtration to give colorless powder crystals. The obtained crystals were combined and recrystallized from ethanol-ethyl acetate to give the title compound (22.1 g) as colorless powder crystals.

$^1$H-NMR (CDCl$_3$+CD$_3$OD) δ: 2.89–3.02 (2H, m), 3.04 (3H, s), 4.12–4.25 (1H, m), 4.27–4.43 (1H, m), 6.79 (1H, s), 7.20 (1H, q, J=4.6 Hz), 7.54 (1H, s), 7.63 (1H, dd, J=1.8 Hz, 8.6 Hz), 7.83 (2H, s), 7.89 (1H, d, J=8.6 Hz), 8.03 (1H, s), 8.28 (1H, s).

IR (KBr): 3500–3000, 1644, 1605, 1559, 1497, 1464, 1318, 1082 cm$^{-1}$.

Example 19

Production of 8-(6-methoxy-2-naphthtyl)-5,6,7,8-tetrahydroimidazo[1,5-a]pyridin-8-ol

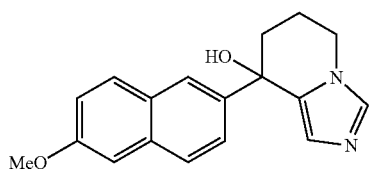

Under an argon atmosphere, 2-bromo-6-methoxynaphthalene (356 mg) was dissolved in tetrahydrofuran (6 ml) and a hexane solution (1.6 M, 1.0 ml) of n-butyl lithium was added dropwise at −78° C. The mixture was stirred at the same temperature for 30 min and a tetrahydrofuran solution (6 ml) of 6,7-dihydroimidazo[1,5-a]pyridin-8(5H)-one (136 mg) was added dropwise. The reaction mixture was gradually warmed from −78° C. to room temperature and the mixture was stirred for 2 h. The reaction mixture was cooled to −78° C. again, and saturated aqueous ammonium chloride solution (10 ml) was added and extracted with ethyl acetate. The organic layer was washed with water and brine, dried over magnesium sulfate and concentrated under reduced pressure. The residue was purified by silica gel column chromatography (eluent; ethyl acetate:methanol=5:1) and recrystallized from ethyl acetate-diethyl ether to give the title compound (101 mg) as colorless crystals.

$^1$H-NMR(CDCl$_3$) δ: 1.9–2.5 (4H, m), 3.93 (3H, s), 3.95–4.1 (1H, m), 4.2–4.35 (1H, m), 6.75 (1H, s), 7.1–7.2 (2H, m), 7.45–7.55 (2H, m) 7.65–7.75 (2H, m), 7.92 (1H, s).

IR(KBr): 1485, 1387, 1265, 1202, 1028, 856 cm$^{-1}$.

Example 20

Production of 8-(4'-fluoro-1,1'-biphenyl-4-yl)-5,6,7,8-tetrahydroimidazo[1,5-a]pyridin-8-ol

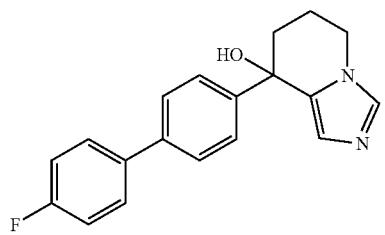

(i) Production of 8-(4-bromophenyl)-5,6,7,8-tetrahydroimidazo-[1,5-a]pyridin-8-ol The reactions in the same manner as in Example 19 using 1,4-dibromobenzene (4.53 g), a hexane solution (1.6 M; 10.0 ml) of n-butyl lithium and 6,7-dihydroimidazo[1,5-a]pyridin-8(5H)-one (1.09 g) afforded the title compound (916 mg) as a pale-yellow powder.

$^1$H-NMR(CDCl$_3$) δ: 1.85–2.05 (2H, m), 2.1–2.25 (1H, m), 2.3–2.5 (1H, m), 3.85–4.05 (1H, m), 4.15–4.3 (1H, m), 6.67 (1H, s), 7.36 (2H, d, J=8.8 Hz), 7.46 (2H, d, J=8.8 Hz), 7.47 (1H, s).

IR(KBr): 1485, 1453, 1397, 1208, 1105, 953, 936, 831, 812 cm$^{-1}$.

(ii) Production of 8-(4'-fluoro-1,1'-biphenyl-4-yl)-5,6,7,8-tetrahydroimidazo[1,5-a]pyridin-8-ol 4-Phenylboric acid (285 mg) and 8-(4-bromophenyl)-5,6,7,8-tetrahydroimidazo[1,5-a]pyridin-8-ol (400 mg) were suspended in a toluene (6 ml)-ethanol (1 ml) mixture, and 2N aqueous sodium carbonate solution (1.36 ml) and tetrakistriphenylphosphine palladium (52 mg) were added under an argon atmosphere. The mixture was stirred at 90° C. for 16 h. Water (20 ml) was added and the mixture was extracted with an ethyl acetate-tetrahydrofuran mixture. The organic layer was washed with brine, dried over magnesium sulfate and concentrated under reduced pressure. The residue was purified by silica gel column chromatography (eluent; ethyl acetate:methanol=5:1) and recrystallized from an ethyl acetate-methanol-diethyl ether mixture to give the title compound (195 mg) as colorless crystals.

$^1$H-NMR(CDCl$_3$) δ: 1.9–2.6 (4H, m), 3.9–4.1 (1H, m), 4.2–4.35 (1H, m), 6.76 (1H, s), 7.13 (2H, t, J=8.8 Hz), 7.45–7.65 (7H, m).

IR(KBr): 1497, 1240, 1213, 1105, 990, 814 cm$^{-1}$.

Example 21

Production of N-[4'-(8-hydroxy-5,6,7,8-tetrahydroimidazo[1,5-a]pyridin-8-yl)-1,1'-biphenyl-3-yl]acetamide

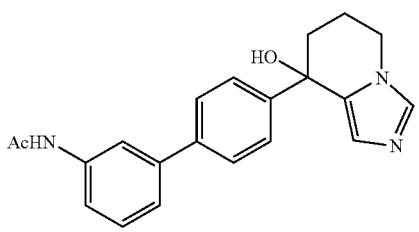

The reactions in the same manner as in Example 20-(ii) using 3-acetylaminophenylboric acid (365 mg), 8-(4-bromophenyl)-5,6,7,8-tetrahydroimidazo[1,5-a]pyridin-8-ol (400 mg), 2N aqueous sodium carbonate solution (1.36 ml) and tetrakis(triphenylphosphine)palladium (52 mg) afforded the title compound (77 mg) as pale yellow crystals.

$^1$H-NMR(CDCl$_3$) δ: 1.9–2.5 (4H, m), 2.20 (3H, s), 3.9–4.1 (1H, m), 4.15–4.3 (1H, m), 6.75 (1H, s), 7.3–7.6 (8H, m), 7.72 (1H, s).

IR(KBr): 1669, 1557, 1483, 1395, 1107, 791 cm$^{-1}$.

Example 22

Production of tert-butyl 3-{6-[(diisonronylamino)carbonyl]-2-naphthtyl}-3(S)-hydroxy-3-(1-trityl-1H-imidazol-4-yl)propionate

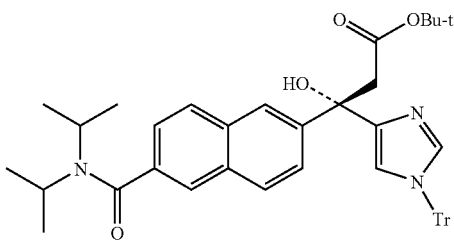

Zinc powder (1.04 g) was suspended in dry THF (8 ml) and chlorotrimethylsilane (0.1 ml) was added at room temperature. The mixture was stirred for 20 min. The reaction mixture was heated to 50° C., and while maintaining the reaction temperature at not more than 60° C., tert-butyl bromoacetate (2.36 ml) was added dropwise over 20 min. The mixture was stirred at 60° C. for 20 min and allowed to cool to give a solution of Reformatsky reagent.

Cinchonine (1.55 g) was suspended in dry THF (10 ml) and Reformatsky reagent (0.35 M; 48.2 ml) and pyridine (1.37 ml) were added dropwise under ice-cooling. The mixture was stirred under ice-cooling for 20 min and cooled in a dry ice-acetonitrile bath to −42° C. Then, a dry THF (20 ml) solution of N,N-diisopropyl-6-[(1-trityl-1H-imidazol-4-yl)carbonyl]-2-naphthamide (2.50 g) was added dropwise over 10 min. The mixture was stirred at the same temperature for 4 h, 1N hydrochloric acid was added and extracted with ethyl acetate. The mixture was washed with 1N hydrochloric acid (twice), water, saturated aqueous sodium bicarbonate solution and saturated brine and dried over magnesium sulfate. The solvent was evaporated and the residue was purified by flash chromatography (eluent; hexane:ethyl acetate=3:1→2:1) to give the title compound (2.93 g) as a colorless amorphous.

$^1$H-NMR(CDCl$_3$) δ: 1.31 (9H, s), 1.0–1.6 (12H, br d), 3.12 (1H, d, J=16.0 Hz), 3.40 (1H, d, J=16.0 Hz), 3.69 (2H, br s), 5.26 (1H, s), 6.86 (1H, d, J=1.8 Hz), 7.07–7.12 (6H, m), 7.25–7.32 (9H, m), 7.36–7.39 (2H, m), 7.70 (1H, dd, J=1.8 Hz, 8.7 Hz), 7.73–7.78 (2H, m), 7.82 (1H, d, J=8.4 Hz), 8.03 (1H, s).

IR: 3462, 2972, 1732, 1705, 1634, 1445, 1369, 1337, 1159 cm$^{-1}$.

enantiomer excess: 92% ee

HPLC Analysis Conditions column: Chiralpak AD mobile phase: hexane:ethanol=85:15 flow rate: 0.8 ml/min detection: UV (254 nm)

Preparation Example 1

| capsule | |
| --- | --- |
| (1) compound obtained in Example 2 | 10 mg |
| (2) lactose | 90 mg |
| (3) microcrystalline cellulose | 70 mg |
| (4) magnesium stearate | 10 mg |
| 1 capsule | 180 mg |

The entire amount of the above-mentioned (1), (2) and (3) and 5 mg of (4) were admixed, granulated and 5 mg of the remaining (4) was added. The entire mass was encapsulated in a gelatin capsule.

Preparation Example 2

| tablet | |
| --- | --- |
| (1) compound obtained in Example 11 | 10 mg |
| (2) lactose | 35 mg |
| (3) corn starch | 150 mg |
| (4) microcrystalline cellulose | 30 mg |
| (5) magnesium stearate | 5 mg |
| 1 tablet | 230 mg |

The entire amount of the above-mentioned (1), (2) and (3), 20 mg of (4) and 2.5 mg of (5) were admixed, granulated and 10 mg of the remaining (4) and 2.5 mg of (5) were added. The mixture was compression formed to give a tablet.

Experimental Example 1

Assay of steroid C$_{17,20}$-Lyase-Inhibitory Activity in Rat

The assay was performed according to The Prostate, Vol. 26, 140–150 (1995).

The orchis was removed from 13-week-old male SD rat. The orchis was homogenized and centrifuged to prepare a microsome. The [1.2-$^3$H]-17α-hydroxyprogesterone having a final concentration of 10 nM, NADPH solution and the test compound were dissolved in a 100 mM phosphate buffer solution (10 μl, pH 7.4). Microsome protein (7 μg/10 μl) was added and the mixture was incubated at 37° C. for 7 min.

Ethyl acetate (40 μl) was added and the mixture was centrifuged, and the substrate and the product (androstenedione and testosterone) in the supernatant were separated by a silica gel thin layer chromatography (TLC). The spot was detected and quantitatively assayed by a BAS 2000 bioimage analyzer. Taking the production amount when the test compound was not added (control) as 100%, the concentration ($IC_{50}$) of the compound necessary for 50% inhibition of the product amount relative to the control was calculated. The results are shown in Table 1.

TABLE 1

| test compound | | $IC_{50}$ (nM) |
|---|---|---|
| Example 3 | 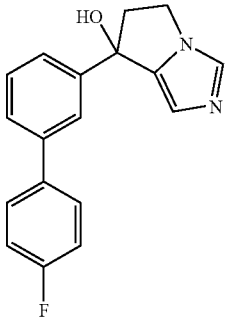 | 10 |
| Example 4 | 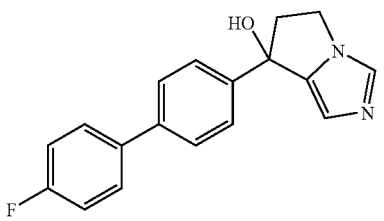 | 25 |
| Example 5 | 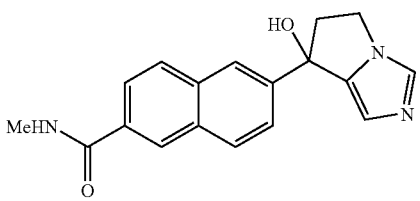 | 54 |
| Example 11 | 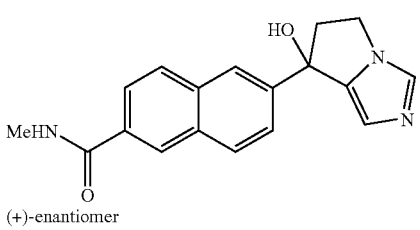 (+)-enantiomer | 48 |

Experimental Example 2

Assay of Inhibitory Effect on Testosterone Biosynthesis in Rats

The test compound (25 mg/kg) was orally administered to 9-week-old male SD (Sprague Dawley) rat. Blood was taken at 2 h after administration of the compound and the concentration of testosterone in the obtained serum was assayed by radioimmunoassay. The proportion (T/C, %) of testosterone concentration of the test drug administration group relative to the testosterone concentration of the control group was calculated to determine testosterone synthesis-inhibitory activity. The results are shown in Table 2.

TABLE 2

| test compound | | inhibitory effect on testosterone biosynthesis (T/C, %) |
|---|---|---|
| Example 3 | 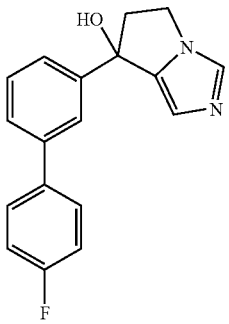 | 4.4 |

Experimental Example 3

Assay of Human CYP3A4-Inhibitory Activity

Performed as in the following according to Journal of Biological Chemistry, vol. 256, 11937 (1983).

A phosphate buffer solution (50 mM, pH 7.4) containing testosterone (final concentration 100 μM, hereinafter the same), human CYP3A4 (10 pmol/ml, manufactured by GENTEST), NADPH producing system (0.5 mM NADP, 5 mM glucose-6-phosphate, 5 mM magnesium chloride, 1.5 units/ml glucose-6-phosphate dehydrogenase) and the test compound was incubated at 37° C. for 30 min. Acetonitrile was added to the reaction mixture and the mixture was stirred and centrifuged. The 6β-hydroxytestosterone in the obtained supernatant was analyzed by high performance liquid chromatography. The concentration ($IC_{50}$) of the compound necessary for 50% inhibition was calculated taking the production amount without addition of the test compound as 100%. The results are shown in Table 3.

TABLE 3

| test compound | | $IC_{50}$ (μM) |
|---|---|---|
| Example 3 | 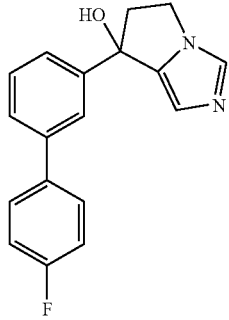 | 9.6 |

TABLE 3-continued

| test compound | | IC$_{50}$ (μM) |
|---|---|---|
| Example 4 | 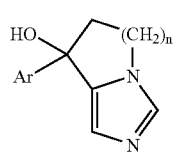 | >10 |
| Example 5 | | >10 |
| Reference Example 11 | | <1.0 |

INDUSTRIAL APPLICABILITY

The compound of the present invention and a salt thereof have a steroid C$_{17,20}$-lyase-inhibitory activity and are useful for the therapy and prophylaxis of various diseases such as primary cancer, metastasis or recrudescence of malignant tumor affected by sex steroid and metabolites thereof, various symptoms associated with these cancers, prostatic hypertrophy, masculinism, hypertrichosis, male type baldness, male infant-type prematurity, endometriosis, hysteromyoma, mastopathy, polycystic ovary syndrome and the like in mammals.

This application is based on patent application Nos. 351780/2000, 247618/2001 and 336880/2001 filed in Japan, the contents of which are hereby incorporated by reference.

The invention claimed is:

1. A compound of the formula:

(I)

wherein n is 1 and

Ar is a group of the formula:

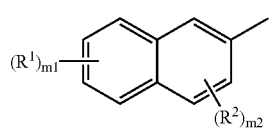

(1)

wherein m1 is an integer of 1 to 4, m2 is an integer of 0 to 3,

R$^1$ and R$^2$ are the same or different and each is independently a hydrogen atom, an optionally substituted hydroxyl group, an optionally substituted thiol group, an optionally substituted amino group, an acyl group, a halogen atom or an optionally substituted hydrocarbon group, a group of the formula:

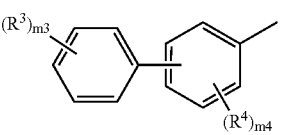

(2)

wherein m3 is an integer of 1 to 5, m4 is an integer of 0 to 4,

R$^3$ and R$^4$ are the same or different and each is independently a hydrogen atom, an optionally substituted hydroxyl group, an optionally substituted thiol group, an optionally substituted amino group, an acyl group, a halogen atom or an optionally substituted hydrocarbon group, or a group of the formula:

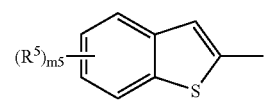

(3)

wherein m5 is an integer of 1 to 4 and

R$^5$ is hydrogen atom, an optionally substituted hydroxyl group, an optionally substituted thiol group, an optionally substituted amino group, an acyl group, a halogen atom or an optionally substituted hydrocarbon group, or a salt thereof or a prodrug thereof.

2. The compound of claim 1, wherein Ar is a group of the formula:

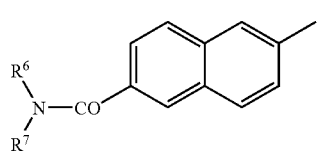

(1-1)

wherein $R^6$ and $R^7$ are the same or different and each is independently a hydrogen atom or a lower alkyl group, or a group of the formula:

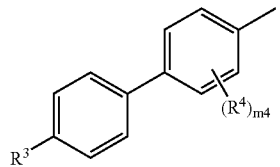

(2-1)

wherein m4 is an integer of 0 to 4, $R^3$ and $R^4$ are the same or different and each is independently a hydrogen atom, an optionally substituted hydroxyl group, an optionally substituted thiol group, an optionally substituted amino group, an acyl group, a halogen atom or an optionally substituted hydrocarbon group.

3. The compound of claim 1, wherein Ar is a group of the formula:

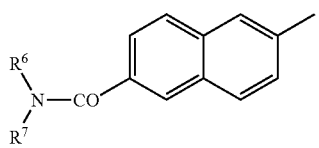

(1-1)

wherein $R^6$ and $R^7$ are the same or different and each is independently a hydrogen atom or lower alkyl group.

4. The compound of claim 1, wherein the compound of the formula (I) is selected from the group consisting of the following compounds:
(±)-7-(5-methoxybenzo[b]thiophen-2-yl)-6,7-dihydro-5H-pyrrolo[1,2-c]imidazol-7-ol,
(±)-7-(5-fluorobenzo[b]thiophen-2-yl)-6,7-dihydro-5H-pyrrolo[1,2-c]imidazol-7-ol,
(±)-7-(4'-fluoro[1,1'-biphenyl]-3-yl)-6,7-dihydro-5H-pyrrolo[1,2-c]imidazol-7-ol,
(±)-7-(4'-fluoro[1,1'-biphenyl]-4-yl)-6,7-dihydro-5H-pyrrolo[1,2-c]imidazol-7-ol,
(±)-6-(7-hydroxy-6,7-dihydro-5H-pyrrolo[1,2-c]imidazol-7-yl)-N-methyl-2-naphthamide,
(±)-N-ethyl-6-(7-hydroxy-6,7-dihydro-5H-pyrrolo[1,2-c]imidazol-7-yl)-2-naphthamide,
(±)-6-(7-hydroxy-6,7-dihydro-5H-pyrrolo[1,2-c]imidazol-7-yl)-N-isopropyl-2-naphthamide, and
(±)-6-(7-hydroxy-6,7-dihydro-5H-pyrrolo[1,2-c]imidazol-7-yl)-2-naphthamide.

5. The compound of claim 1, which is an enantiomer wherein the steric configuration is an S configuration.

6. The compound of claim 1, which is an enantiomer wherein the steric configuration is an R configuration.

7. The compound of claim 1, wherein the compound of the formula (I) is selected from the group consisting of the following compounds:
(±)-7-(4'-fluoro[1,1'-biphenyl]-3-yl)-6,7-dihydro-5H-pyrrolo[1,2-c]imidazol-7-ol,
(±)-7-(4'-fluoro[1,1'-biphenyl]-4-yl)-6,7-dihydro-5H-pyrrolo[1,2-c]imidazol-7-ol,
(±)-6-(7-hydroxy-6,7-dihydro-5H-pyrrolo[1,2-c]imidazol-7-yl)-N-methyl-2-naphthamide, and
(±)-6-(7-hydroxy-6,7-dihydro-5H-pyrrolo[1,2-c]imidazol-7-yl)-2-naphthamide.

8. The compound of claim 1, wherein the compound of the formula (I) is selected from the group consisting of the following compounds:
(+)-7-(4'-fluoro[1,1'-biphenyl]-3-yl)-6,7-dihydro-5H-pyrrolo[1,2-c]imidazol-7-ol,
(−)-7-(4'-fluoro[1,1'-biphenyl]-3-yl)-6,7-dihydro-5H-pyrrolo[1,2-c]imidazol-7-ol,
(+)-7-(4'-fluoro[1,1'-biphenyl]-4-yl)-6,7-dihydro-5H-pyrrolo[1,2-c]imidazol-7-ol,
(−)-7-(4'-fluoro[1,1'-biphenyl]-4-yl)-6,7-dihydro-5H-pyrrolo[1,2-c]imidazol-7-ol,
(+)-6-(7-hydroxy-6,7-dihydro-5H-pyrrolo[1,2-c]imidazol-7-yl)-N-methyl-2-naphthamide,
(−)-6-(7-hydroxy-6,7-dihydro-5H-pyrrolo[1,2-c]imidazol-7-yl)-N-methyl-2-naphthamide,
(+)-6-(7-hydroxy-6,7-dihydro-5H-pyrrolo[1,2-c]imidazol-7-yl)-2-naphthamide, and
(−)-6-(7-hydroxy-6,7-dihydro-5H-pyrrolo[1,2-c]imidazol-7-yl)-2-naphthamide.

9. A pharmaceutical composition containing the compound of claim 1 or a prodrug thereof and a pharmaceutically acceptable carrier, excipient or diluent.

10. A diastereomeric salt of a compound of the formula (I-1)

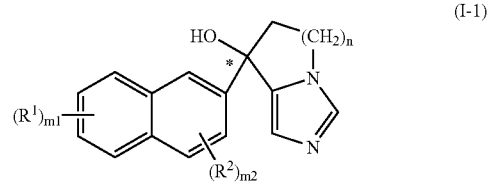

(I-1)

wherein n is 1,
m1 is an integer of 1 to 4,
m2 is an integer of 0 to 3,
$R^1$ and $R^2$ are the same or different and each is independently a hydrogen atom, an optionally substituted hydroxyl group, an optionally substituted thiol group, an optionally substituted amino group, an acyl group, a halogen atom or an optionally substituted hydrocarbon group, and
* shows the position of an asymmetric carbon,
and a compound of the formula (IV)

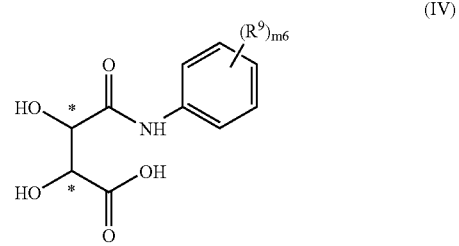

(IV)

wherein each $R^9$ is the same or different and is a hydrogen atom, $C_{1-3}$ alkyl group, $C_{1-3}$ alkoxy group, a hydroxyl group, a nitro group, or a halogen atom,
m6 is an integer of 0 to 3, and
* shows the position of an asymmetric carbon.

11. A diastereomeric salt of a compound of the formula (I-2)

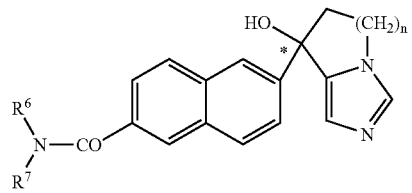

wherein n is 1,

R$^6$ and R$^7$ are the same or different and each is independently a hydrogen atom or a lower alkyl group and \* shows the position of an asymmetric carbon and a compound of the formula (IV)

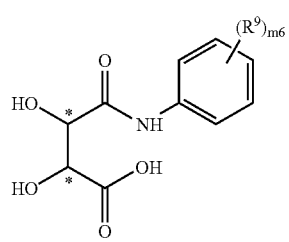

wherein each R$^9$ is the same or different and is a hydrogen atom, C$_{1-3}$ alkyl group, C$_{1-3}$ alkoxy group, a hydroxyl group, a nitro group, or a halogen atom, m6 is an integer of 0 to 3, and \* shows the position of an asymmetric carbon.

12. A diastereomeric salt of 6-(7-hydroxy-6,7-dihydro-5H-pyrrolo[1,2-c]imidazol-7-yl)-N-methyl-2-naphthamide and an optically active tartranilic acid.

13. A salt of (+)-6-(7-hydroxy-6,7-dihydro-5H-pyrrolo[1,2-c]unidazol-7 -yl)-N-methyl-2-naphthamide and (2S,3 S)-(−)-tartranilic acid.

14. A pharmaceutical composition containing, as an active ingredient, an optically active compound of the compound of the formula (I-1)

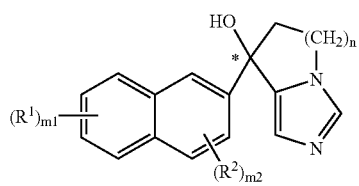

wherein n is 1,
m1 is an integer of 1 to 4,
m2 is an integer of 0 to 3,
R$^1$ and R$^2$ are the same or different and each is independently a hydrogen atom, an optionally substituted hydroxyl group, an optionally substituted thiol group, an optionally substituted amino group, an acyl group, a halogen atom or an optionally substituted hydrocarbon group, and \* shows the position of an asymmetric carbon and a pharmaceutically acceptable carrier, excipient or diluent.

15. A pharmaceutical composition containing the compound or a prodrug thereof of claim 2 and a pharmaceutically acceptable carrier, excipient or diluent.

16. A pharmaceutical composition containing the compound or a prodrug thereof of claim 3 and a pharmaceutically acceptable carrier, excipient or diluent.

17. A pharmaceutical composition containing the compound or a prodrug thereof of claim 4 and a pharmaceutically acceptable carrier, excipient or diluent.

18. A pharmaceutical composition containing the compound or a prodrug thereof of claim 5 and a pharmaceutically acceptable carrier, excipient or diluent.

19. A pharmaceutical composition containing the compound or a prodrug thereof of claim 6 and a pharmaceutically acceptable carrier, excipient or diluent.

20. A pharmaceutical composition containing the compound or a prodrug thereof of claim 7 and a pharmaceutically acceptable carrier, excipient or diluent.

21. A pharmaceutical composition containing the compound or a prodrug thereof of claim 8 and a pharmaceutically acceptable carrier, excipient or diluent.

\* \* \* \* \*

UNITED STATES PATENT AND TRADEMARK OFFICE
CERTIFICATE OF CORRECTION

| | | |
|---|---|---|
| PATENT NO. | : 7,141,598 B2 | Page 1 of 1 |
| APPLICATION NO. | : 10/416986 | |
| DATED | : November 28, 2006 | |
| INVENTOR(S) | : Akihiro Tasaka et al. | |

It is certified that error appears in the above-identified patent and that said Letters Patent is hereby corrected as shown below:

In Claim 7, Column 55, at line 62:

It should read: (+)-7-(4'-fluoro[1,1'-biphenyl]-4-yl)-6,7-dihydro-5H-

In Claim 13, Column 57, at line 47:

It should read: 2-c]imidazol-7-yl)-N-methyl-2-naphthamide and (2S,<u>3S</u>)-

Signed and Sealed this

Twenty-sixth Day of June, 2007

JON W. DUDAS
*Director of the United States Patent and Trademark Office*